( 12 ) United States Patent
Hariton et al.

(10) Patent No.: US 10,856,972 B2
(45) Date of Patent: Dec. 8, 2020

(54) PROSTHETIC VALVE WITH ANGULARLY OFFSET ATRIAL ANCHORING ARMS AND VENTRICULAR ANCHORING LEGS

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 116 days.

(21) Appl. No.: 16/136,110

(22) Filed: Sep. 19, 2018

(65) Prior Publication Data

US 2019/0083252 A1 Mar. 21, 2019

Related U.S. Application Data

(60) Provisional application No. 62/560,384, filed on Sep. 19, 2017.

(51) Int. Cl.
*A61F 2/24* (2006.01)

(52) U.S. Cl.
CPC ............ *A61F 2/2418* (2013.01); *A61F 2/243* (2013.01); *A61F 2/2436* (2013.01);
(Continued)

(58) Field of Classification Search
CPC .... A61F 2/2409; A61F 2/2436; A61F 2/2418; A61F 2/243; A61F 2/246
See application file for complete search history.

(56) References Cited

U.S. PATENT DOCUMENTS

| 5,776,140 A | 7/1998 | Cottone |
| 5,957,949 A | 9/1999 | Leonhardt et al. |

(Continued)

FOREIGN PATENT DOCUMENTS

| EP | 1264582 A2 | 12/2002 |
| WO | WO 2008/029296 A2 | 3/2008 |

(Continued)

OTHER PUBLICATIONS

International Search Report dated Dec. 5, 2011, by the United States Patent arid Trademark Office in PCT/IL2011/000582 (3 pages).

(Continued)

*Primary Examiner* — Brian A Dukert
(74) *Attorney, Agent, or Firm* — Finnegan, Henderson, Farabow, Garrett & Dunner, LLP

(57) ABSTRACT

Prosthetic valves and methods of implanting prosthetic valves may be provided, including a prosthetic valve for implantation within a native heart valve. The prosthetic valve may include an annular valve body, a plurality of atrial anchoring arms, and a plurality of ventricular anchoring legs. The arms and legs may extend radially outward from the annular valve body and may each include a native valve tissue engaging portion. The arms may be angularly offset from the legs, with the tissue engaging portion of each arm and each leg arranged such that when the arms and legs are positioned on opposing sides of native heart valve tissue, the native heart valve tissue may assume a serpentine arrangement between the arms and the legs.

24 Claims, 21 Drawing Sheets

(52) U.S. Cl.
CPC .......... *A61F 2/2445* (2013.01); *A61F 2/2454* (2013.01); *A61F 2/2463* (2013.01); *A61F 2/246* (2013.01); *A61F 2/2409* (2013.01); *A61F 2/2466* (2013.01); *A61F 2210/0014* (2013.01); *A61F 2220/0008* (2013.01); *A61F 2250/007* (2013.01)

(56) References Cited

U.S. PATENT DOCUMENTS

| | | |
|---|---|---|
| 6,010,530 A | 1/2000 | Goicoechea |
| 6,402,780 B2 | 6/2002 | Williamson, IV et al. |
| 6,458,153 B1 | 10/2002 | Bailey et al. |
| 6,669,724 B2 | 12/2003 | Park et al. |
| 6,733,525 B2 | 5/2004 | Yang et al. |
| 7,201,772 B2 | 4/2007 | Schwammenthal et al. |
| 7,442,204 B2 | 10/2008 | Schwammenthal et al. |
| 7,837,727 B2 | 11/2010 | Goetz et al. |
| 7,959,672 B2 | 6/2011 | Salahieh et al. |
| D652,927 S | 1/2012 | Braido et al. |
| D653,341 S | 1/2012 | Braido et al. |
| 8,109,996 B2 | 2/2012 | Stacchino et al. |
| D660,433 S | 5/2012 | Braido et al. |
| D660,967 S | 5/2012 | Braido et al. |
| 8,313,525 B2 | 11/2012 | Tuval et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,579,964 B2 | 11/2013 | Lane et al. |
| 8,628,571 B1 | 1/2014 | Hacohen et al. |
| 8,652,203 B2 | 2/2014 | Quadri et al. |
| 8,657,872 B2 | 2/2014 | Seguin |
| 8,728,155 B2 | 5/2014 | Montorfano et al. |
| 8,747,460 B2 | 6/2014 | Tuval et al. |
| 8,784,481 B2 | 7/2014 | Alkhatib et al. |
| 8,852,272 B2 | 10/2014 | Gross et al. |
| 8,870,948 B1 | 10/2014 | Erzberger et al. |
| 8,870,950 B2 | 10/2014 | Hacohen |
| 8,961,595 B2 | 2/2015 | Alkhatib |
| 8,986,375 B2 | 3/2015 | Garde et al. |
| 8,992,604 B2 | 3/2015 | Hacohen et al. |
| 8,998,982 B2 | 4/2015 | Richter et al. |
| 9,017,399 B2 | 4/2015 | Hacohen et al. |
| D730,520 S | 5/2015 | Braido et al. |
| D730,521 S | 5/2015 | Braido et al. |
| 9,023,100 B2 | 5/2015 | Quadri et al. |
| D732,666 S | 6/2015 | Nguyen et al. |
| 9,050,188 B2 | 6/2015 | Schweich, Jr. et al. |
| 9,072,603 B2 | 7/2015 | Tuval et al. |
| 9,095,434 B2 | 8/2015 | Rowe |
| 9,125,740 B2 | 9/2015 | Morriss et al. |
| 9,132,009 B2 | 9/2015 | Hacohen et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,295,552 B2 | 3/2016 | McLean et al. |
| D755,384 S | 5/2016 | Pesce et al. |
| 9,345,573 B2 | 5/2016 | Nyuli et al. |
| 9,387,078 B2 | 7/2016 | Gross et al. |
| 9,439,757 B2 | 9/2016 | Wallace et al. |
| 9,445,893 B2 | 9/2016 | Vaturi |
| 9,492,273 B2 | 11/2016 | Wallace et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,572,665 B2 | 2/2017 | Lane et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,763,657 B2 | 9/2017 | Hacohen et al. |
| D800,908 S | 10/2017 | Hariton et al. |
| 9,788,941 B2 | 10/2017 | Hacohen |
| 9,974,651 B2 | 5/2018 | Hariton et al. |
| 10,010,414 B2 | 7/2018 | Cooper et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 10,226,341 B2 | 3/2019 | Gross et al. |
| 10,245,143 B2 | 4/2019 | Gross et al. |
| 10,321,995 B1 | 6/2019 | Christianson et al. |
| 10,327,895 B2 | 6/2019 | Lozonschi et al. |
| 10,357,360 B2 | 7/2019 | Hariton et al. |
| 10,376,361 B2 | 8/2019 | Gross et al. |
| 10,390,952 B2 | 8/2019 | Hariton et al. |
| 10,426,610 B2 | 10/2019 | Hariton et al. |
| 10,463,487 B2 | 11/2019 | Hariton et al. |
| 10,463,488 B2 | 11/2019 | Hariton et al. |
| 10,507,105 B2 | 12/2019 | Hariton et al. |
| 10,524,903 B2 | 1/2020 | Hariton et al. |
| 10,531,872 B2 | 1/2020 | Hacohen et al. |
| 10,548,731 B2 | 2/2020 | Lashinski et al. |
| 10,667,908 B2 | 6/2020 | Hariton et al. |
| 2004/0186558 A1 | 9/2004 | Pavcnik et al. |
| 2004/0210304 A1 | 10/2004 | Seguin et al. |
| 2004/0249433 A1 | 12/2004 | Freitag |
| 2005/0137697 A1 | 6/2005 | Salahieh et al. |
| 2005/0240200 A1 | 10/2005 | Bergheim |
| 2006/0004469 A1 | 1/2006 | Sokel |
| 2006/0020327 A1 | 1/2006 | Lashinski et al. |
| 2006/0052867 A1 | 3/2006 | Revuelta et al. |
| 2006/0259137 A1 | 11/2006 | Artof et al. |
| 2007/0056346 A1 | 3/2007 | Spenser et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2008/0071361 A1 | 3/2008 | Tuval et al. |
| 2008/0071369 A1 | 3/2008 | Tuval et al. |
| 2008/0082166 A1 | 4/2008 | Styrc et al. |
| 2008/0132989 A1 | 6/2008 | Snow et al. |
| 2008/0147182 A1 | 6/2008 | Righini et al. |
| 2008/0200980 A1 | 8/2008 | Robin et al. |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2009/0281619 A1 | 11/2009 | Le et al. |
| 2010/0023120 A1 | 1/2010 | Holecek et al. |
| 2010/0049313 A1 | 2/2010 | Alon et al. |
| 2010/0100167 A1 | 4/2010 | Bortlein et al. |
| 2010/0161036 A1 | 6/2010 | Pintor et al. |
| 2010/0256737 A1 | 10/2010 | Pollock et al. |
| 2010/0312333 A1 | 12/2010 | Navia et al. |
| 2010/0331971 A1 | 12/2010 | Keränen et al. |
| 2011/0004299 A1 | 1/2011 | Navia et al. |
| 2011/0029072 A1 | 2/2011 | Gabbay |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0224785 A1 | 9/2011 | Hacohen |
| 2011/0245911 A1 | 10/2011 | Quill et al. |
| 2011/0264196 A1 | 10/2011 | Savage et al. |
| 2011/0313515 A1 | 12/2011 | Quadri et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0059458 A1 | 3/2012 | Buchbinder |
| 2012/0065464 A1 | 3/2012 | Ellis et al. |
| 2012/0078237 A1 | 3/2012 | Wang et al. |
| 2012/0089223 A1 | 4/2012 | Nguyen et al. |
| 2012/0101571 A1 | 4/2012 | Thambar et al. |
| 2012/0310328 A1 | 12/2012 | Olson et al. |
| 2012/0323316 A1 | 12/2012 | Chau et al. |
| 2013/0018458 A1 | 1/2013 | Yohanan et al. |
| 2013/0046373 A1 | 2/2013 | Cartledge et al. |
| 2013/0144381 A1 | 6/2013 | Quadri et al. |
| 2013/0190861 A1 | 7/2013 | Chau et al. |
| 2013/0261738 A1 | 10/2013 | Clague et al. |
| 2013/0304200 A1 | 11/2013 | McLean et al. |
| 2014/0000112 A1 | 1/2014 | Braido et al. |

(56) References Cited

U.S. PATENT DOCUMENTS

| | | |
|---|---|---|
| 2014/0018915 A1 | 1/2014 | Biadillah et al. |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |
| 2014/0277409 A1 | 9/2014 | Bortlein et al. |
| 2014/0277411 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358224 A1 | 12/2014 | Tegels et al. |
| 2015/0018944 A1 | 1/2015 | O'Connell et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0184098 A1 | 6/2016 | Vaturi |
| 2016/0270911 A1 | 9/2016 | Ganesan et al. |
| 2016/0310268 A1 | 10/2016 | Oba et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0331525 A1 | 11/2016 | Straubinger et al. |
| 2016/0331526 A1 | 11/2016 | Schweich, Jr. et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0209264 A1 | 7/2017 | Chau et al. |
| 2017/0231759 A1 | 8/2017 | Geist et al. |
| 2017/0231766 A1 | 8/2017 | Hariton et al. |
| 2017/0333187 A1 | 11/2017 | Hariton et al. |
| 2017/0367823 A1 | 12/2017 | Hariton et al. |
| 2018/0021129 A1 | 1/2018 | Peterson et al. |
| 2018/0049873 A1 | 2/2018 | Manash et al. |
| 2018/0055630 A1 | 3/2018 | Patel et al. |
| 2018/0153689 A1 | 6/2018 | Maimon et al. |
| 2018/0206983 A1 | 7/2018 | Noe et al. |
| 2018/0250126 A1 | 9/2018 | O'Connor et al. |
| 2018/0250130 A1 | 9/2018 | Hariton et al. |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |
| 2018/0296336 A1 | 10/2018 | Cooper et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0353294 A1 | 12/2018 | Calomeni et al. |
| 2019/0015093 A1 | 1/2019 | Hacohen et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083242 A1 | 3/2019 | Hariton et al. |
| 2019/0083243 A1 | 3/2019 | Hariton et al. |
| 2019/0083246 A1 | 3/2019 | Hariton et al. |
| 2019/0083247 A1 | 3/2019 | Hariton et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0328519 A1 | 10/2019 | Hariton et al. |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000579 A1 | 1/2020 | Manash et al. |
| 2020/0015964 A1 | 1/2020 | Noe et al. |
| 2020/0046497 A1 | 2/2020 | Hariton et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0129294 A1 | 4/2020 | Hariton et al. |

FOREIGN PATENT DOCUMENTS

| | | |
|---|---|---|
| WO | WO 2010/006627 A1 | 1/2010 |
| WO | WO 2010/057262 A1 | 5/2010 |
| WO | WO 2012/011108 A2 | 1/2012 |
| WO | WO 2012/036740 A2 | 3/2012 |
| WO | WO 2012/048035 A2 | 4/2012 |
| WO | WO 2013/059747 A1 | 4/2013 |
| WO | WO 2013/072496 A1 | 5/2013 |
| WO | WO 2013/078497 A1 | 6/2013 |
| WO | WO 2013/175468 A2 | 11/2013 |
| WO | WO 2014/115149 A2 | 7/2014 |
| WO | WO 2014/164364 A1 | 10/2014 |
| WO | WO 2016/016899 A1 | 2/2016 |
| WO | WO 2016/098104 A2 | 6/2016 |
| WO | WO 2016/125160 A1 | 8/2016 |
| WO | WO 2018/025260 A1 | 2/2018 |
| WO | WO 2018/025263 A2 | 2/2018 |
| WO | WO 2018/029680 A1 | 2/2018 |
| WO | WO 2018/039631 A1 | 3/2018 |
| WO | WO 2018/112429 A1 | 6/2018 |
| WO | WO 2018/118717 A1 | 6/2018 |
| WO | WO 2018/131042 A1 | 7/2018 |
| WO | WO 2018/131043 A1 | 7/2018 |
| WO | WO 2019/195860 A2 | 10/2019 |

OTHER PUBLICATIONS

International Search Report dated Mar. 27, 2018, by the European Patent Office in PCT/IL2017/050849 (5 pages).

International Search Report dated May 30, 2016, by the European Patent Office in PCT/IL2016/050125 (6 pages).

International Search Report dated Nov. 24, 2017, by the European Patent Office in PCT/IL2017/050873 (5 pages).

International Search Report dated Oct. 27, 2015, by the European Patent Office in PCT/IL2015/050792 (3 pages).

International Search Report dated Sep. 4, 2014, by the European Patent Office in PCT/IL2014/050087 (6 pages).

(56) References Cited

OTHER PUBLICATIONS

Written Opinion of the International Searching Authority issued by the United States Patent and Trademark Office in PCT/IL2011/000582 (12 pages).
Written Opinion of the International Searching Authority issued by the European Patent Office in PCT/IL2017/050849 (10 pages).
Written Opinion of the International Searching Authority issued by the European Patent Office in PCT/IL2016/050125 (7 pages).
Written Opinion of the International Searching Authority issued by the European Patent Office in PCT/IL2014/050087 (10 pages).
Written Opinion of the International Searching Authority issued by the European Patent Office in PCT/IL2015/050792 (5 pages).
Written Opinion of the International Searching Authority issued by the European Patent Office in PCT/IL2017/050873 (12 pages).

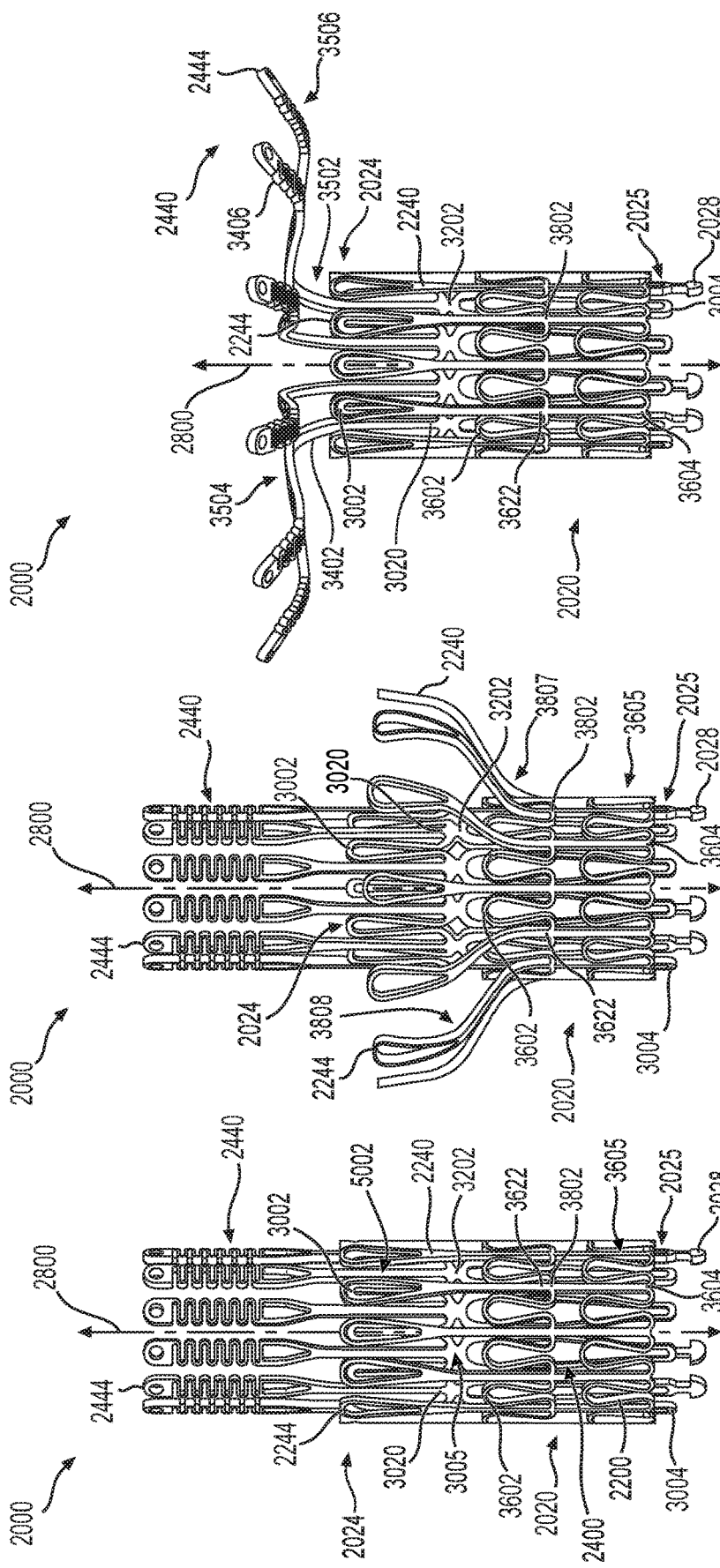

PROSTHETIC VALVE WITH ANGULARLY OFFSET ATRIAL ANCHORING ARMS AND VENTRICULAR ANCHORING LEGS

CROSS-REFERENCE TO RELATED APPLICATION

This application claims priority from U.S. Provisional Patent Application No. 62/560,384, filed Sep. 19, 2017, which is hereby incorporated by reference in its entirety.

TECHNICAL FIELD

This disclosure relates generally to prosthetic valves and delivery systems for prosthetic valves. More specifically, this disclosure relates to prosthetic heart valves and methods thereof.

BACKGROUND

The native heart valves (the tricuspid valve, pulmonary valve, mitral valve, and aortic valve) play an important role in regulating flow of blood through the cardiovascular system. However, the native heart valves may become damaged or impaired due to, for example, cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves that are smaller in size but that are still configured to assist or replace the functionality of a diseased or damaged native heart valve. In addition, there remains a need for prosthetic heart valves that are more easily maneuvered into the heart and securely implanted at the site of a native heart valve. Moreover, there remains a need for improved prosthetic heart valve delivery systems that are configured to securely implant a prosthetic heart valve at an implantation site. The present disclosure provides prosthetic heart valves with a reduced axial length such that the prosthetic heart valves may be more easily delivered into the heart and may exhibit less protrusion into the chambers of the heart. The present disclosure also provides improved prosthetic heart valve delivery systems and methods of implanting prosthetic heart valves, such that prosthetic heart valves may be securely anchored at the implantation site.

SUMMARY

The present disclosure discloses prosthetic valves for implantation within a native heart valve and methods for implanting prosthetic valves within a native heart valve. Particular examples of the disclosure may pertain to a prosthetic valve having atrial anchoring arms and ventricular anchoring legs that are angularly offset and configured to force native valve tissue to assume a serpentine arrangement between the arms and the legs when the prosthetic valve is implanted in a native valve.

According to an exemplary embodiment of the present disclosure, a prosthetic valve for implantation within a native heart valve is provided. The prosthetic valve includes an annular valve body having a tubular annulus. The prosthetic valve also includes a plurality of atrial anchoring arms configured to extend radially outward from the annular valve body. Each of the plurality of atrial anchoring arms includes a native valve tissue engaging portion. The prosthetic valve also includes a plurality of ventricular anchoring legs configured to extend radially outward from the annular valve body. Each of the plurality of ventricular anchoring legs includes a native valve tissue engaging portion. Each of the plurality of atrial anchoring arms is angularly offset from an adjacent leg, with the tissue engaging portion of each arm and each leg being arranged such that when the arms and legs are positioned on opposing sides of the native heart valve tissue, the native heart valve tissue assumes a serpentine arrangement between the arms and the legs.

An entire length of at least one ventricular anchoring leg is configured to extend toward an atrium. At least a portion of at least one atrial anchoring arm is configured to extend toward a ventricle. At least one atrial anchoring arm has a single location of connection to the annular valve body and at least one ventricular anchoring leg has a single location of connection to the annular valve body. The atrial anchoring arms and the ventricular anchoring legs are configured to extend radially outward from separate locations of the annular valve body. A terminal end of at least one atrial anchoring arm is configured to extend in an atrial direction beyond an atrial end of the annular valve body. A terminal end of at least one atrial anchoring arm is configured to be situated in an atrial direction relative to the rest of the at least one atrial anchoring arm. A terminal end of at least one ventricular anchoring leg is configured to be situated in an atrial direction relative to locations of connection of the atrial anchoring arms to the annular valve body. A portion of at least one atrial anchoring arm is configured to extend toward an atrium, the portion of the at least one atrial anchoring arm including the terminal end of the at least one atrial anchoring arm. A portion of at least one ventricular anchoring leg is configured to be substantially aligned in a common lateral plane with a portion of at least one atrial anchoring arm. The portion of the at least one ventricular anchoring leg is a terminal end of the at least one ventricular anchoring leg. A terminal end of the at least one atrial anchoring arm is configured to be situated in an atrial direction relative to the portion of the at least one atrial anchoring arm. The portion of the at least one atrial anchoring arm is situated in an outer radial half of the at least one atrial anchoring arm. A portion of at least one ventricular anchoring leg is configured for placement in an atrial direction relative to at least a portion of at least one atrial anchoring arm. The portion of the at least one atrial anchoring arm is situated in an outer radial half of the at least one atrial anchoring arm. A terminal end of at least one atrial anchoring arm is configured to be situated radially outward from terminal ends of the ventricular anchoring legs. The annular valve body further includes an atrial end, a ventricular end opposite the atrial end, and an intermediate portion extending between the atrial end and the ventricular end. The atrial anchoring arms and the ventricular anchoring legs are configured to extend from the intermediate portion of the annular valve body. The annular valve body additionally includes a plurality of struts intersecting at junctions. The atrial end of the annular valve body includes a plurality of atrial junctions. The ventricular end of the annular valve body includes a plurality of ventricular junctions. The intermediate portion of the annular valve body includes a plurality of intermediate junctions, the atrial anchoring arms and ventricular anchoring legs extending from intermediate junctions. The prosthetic valve additionally includes an annular outer frame and an inner frame situated at least partially within the annular outer frame. The atrial anchoring arms extend from the inner frame and the ventricular anchoring legs extend from the annular outer frame. The inner frame has a greater axial length than a length of the annular outer frame.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIGS. 5A-5E illustrate structural changes in the exemplary frame of FIG. 2A during transitioning of the frame between a radially-contracted configuration and a radially-expanded configuration, consistent with various embodiments of the present disclosure.

DETAILED DESCRIPTION

Figure 1A:
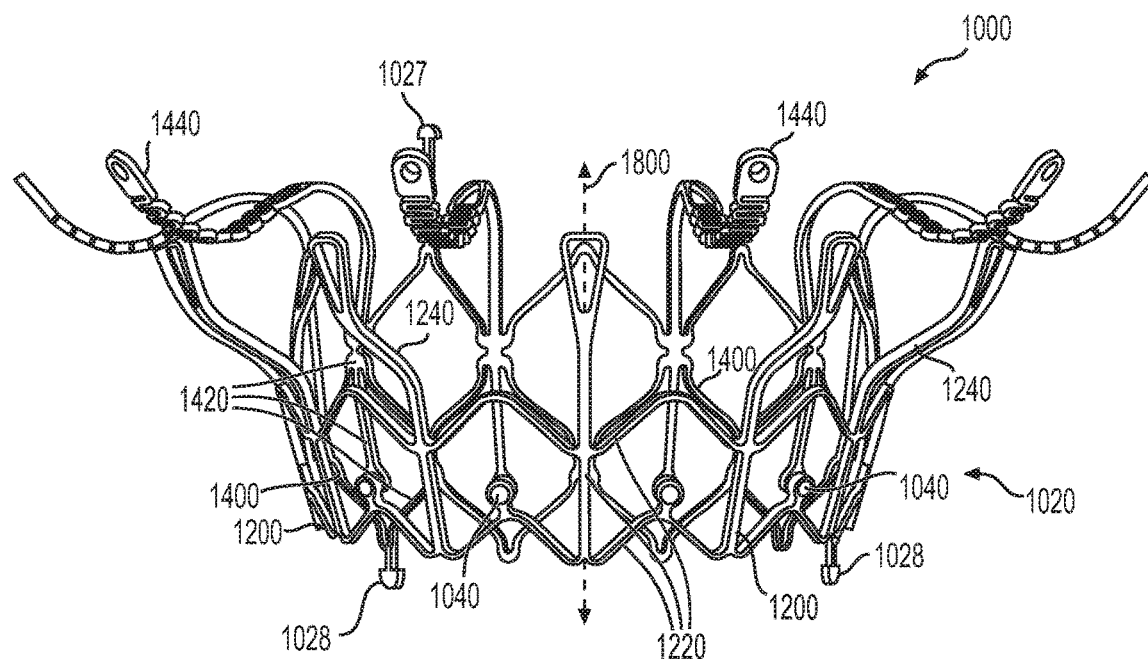
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure non-functional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
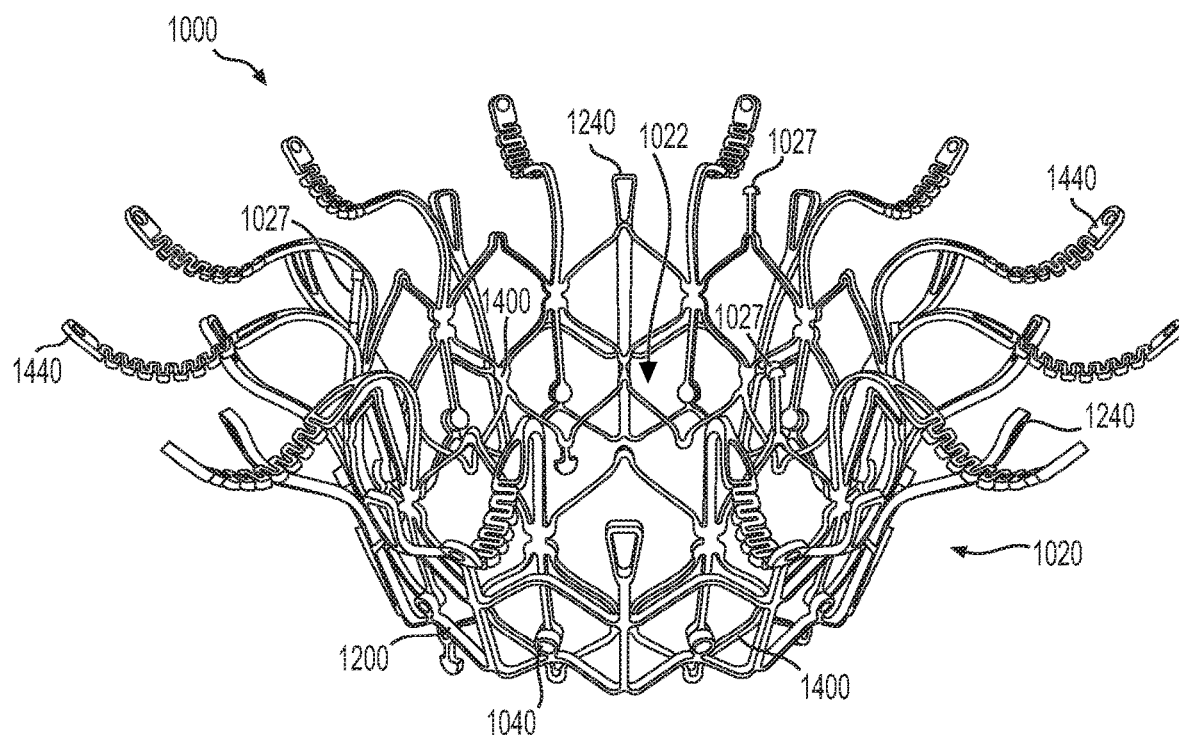
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
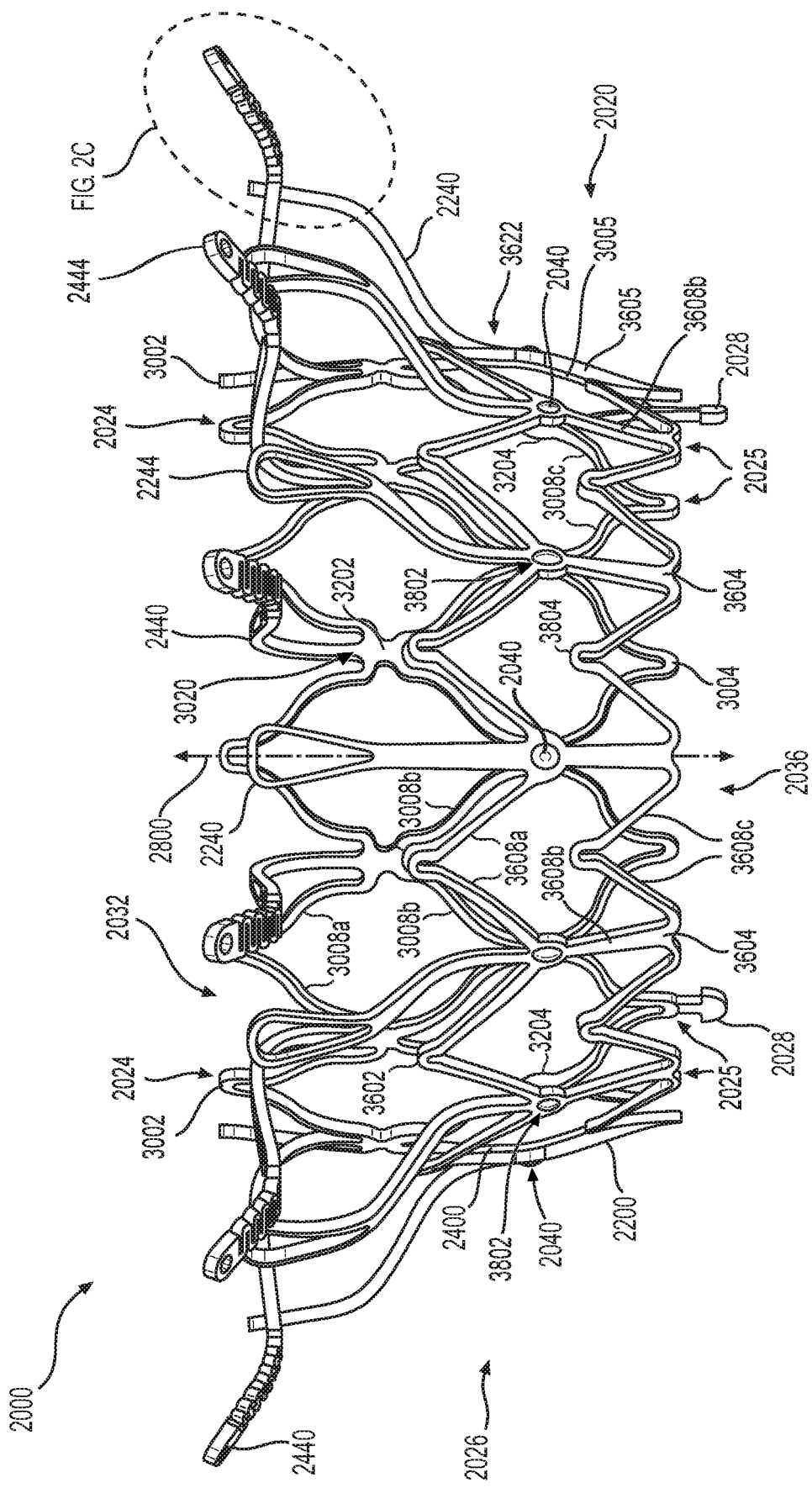
FIG. 2A illustrates a front elevation view of another exemplary frame for a prosthetic valve, consistent with various embodiments of the present disclosure.
Figure 2B:
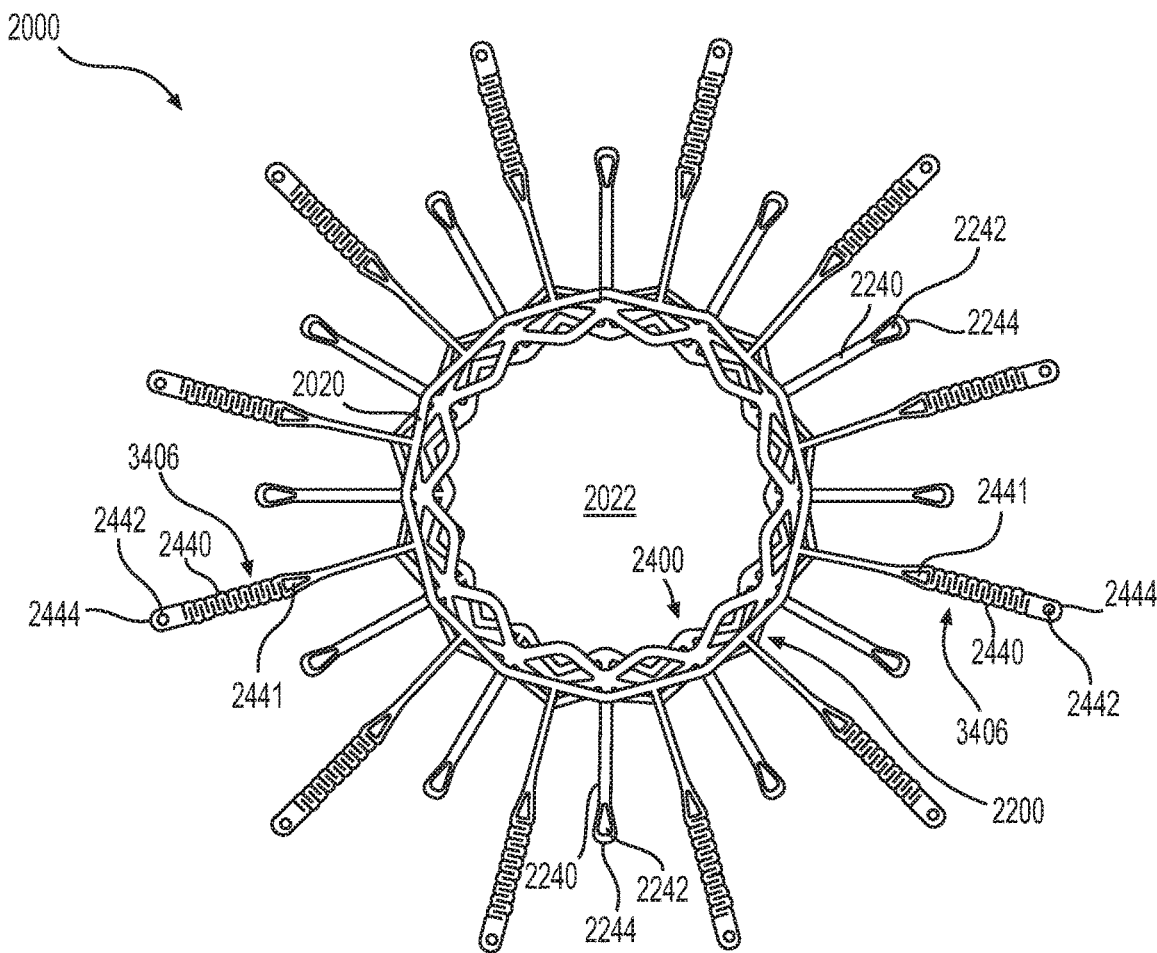
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrim, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
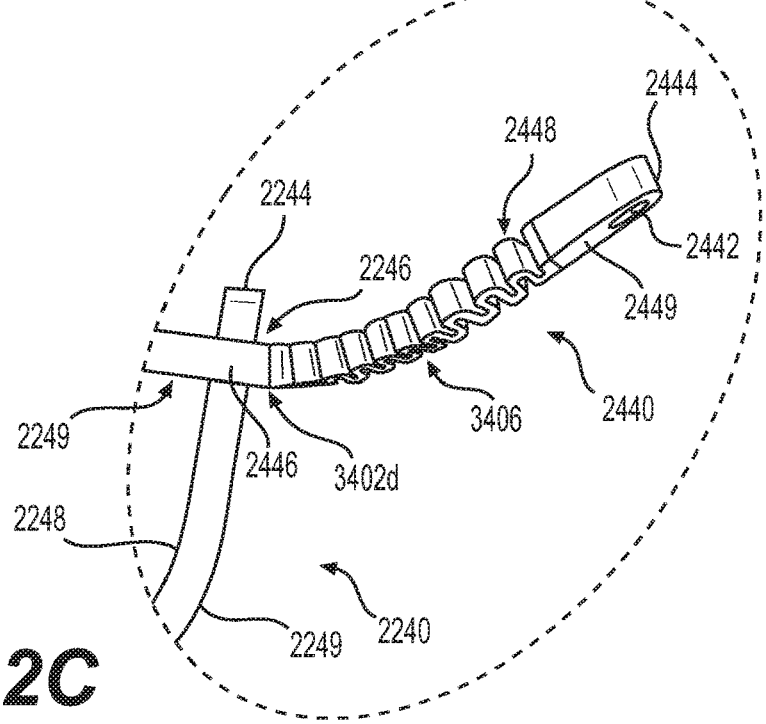
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
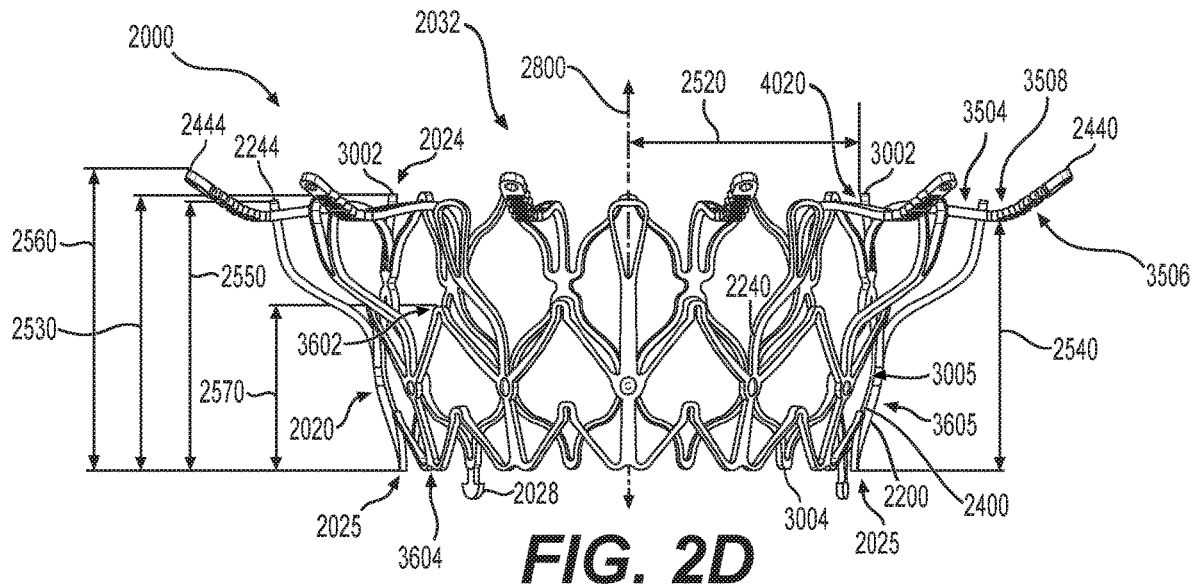
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
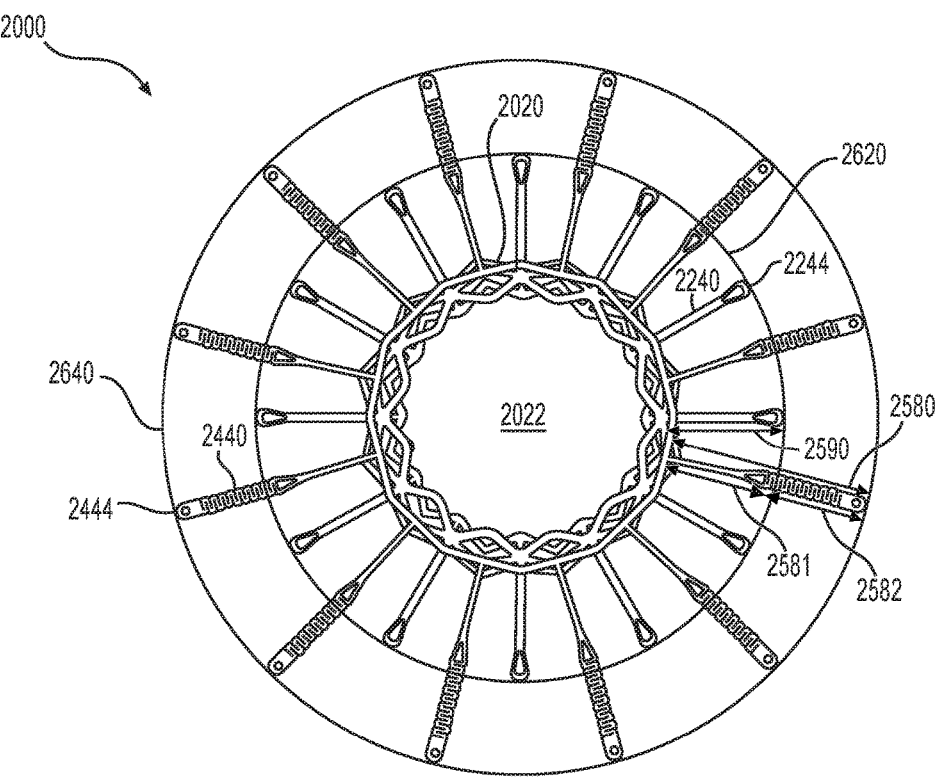
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
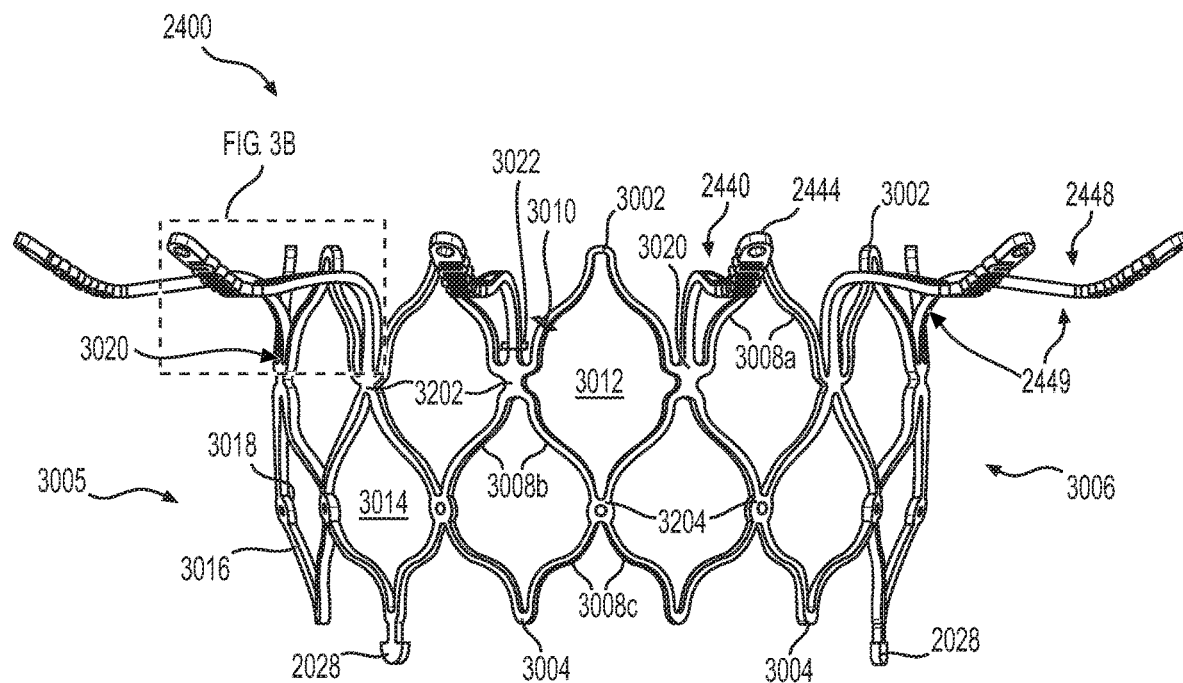
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
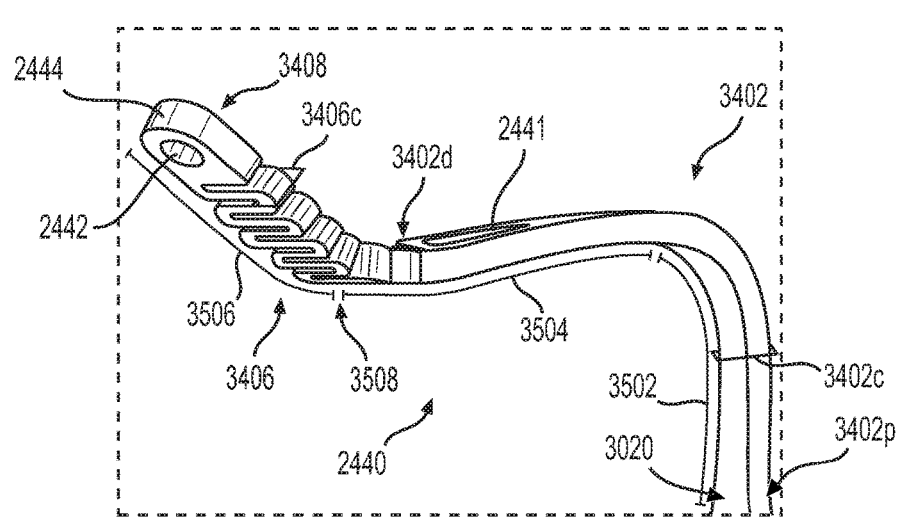
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
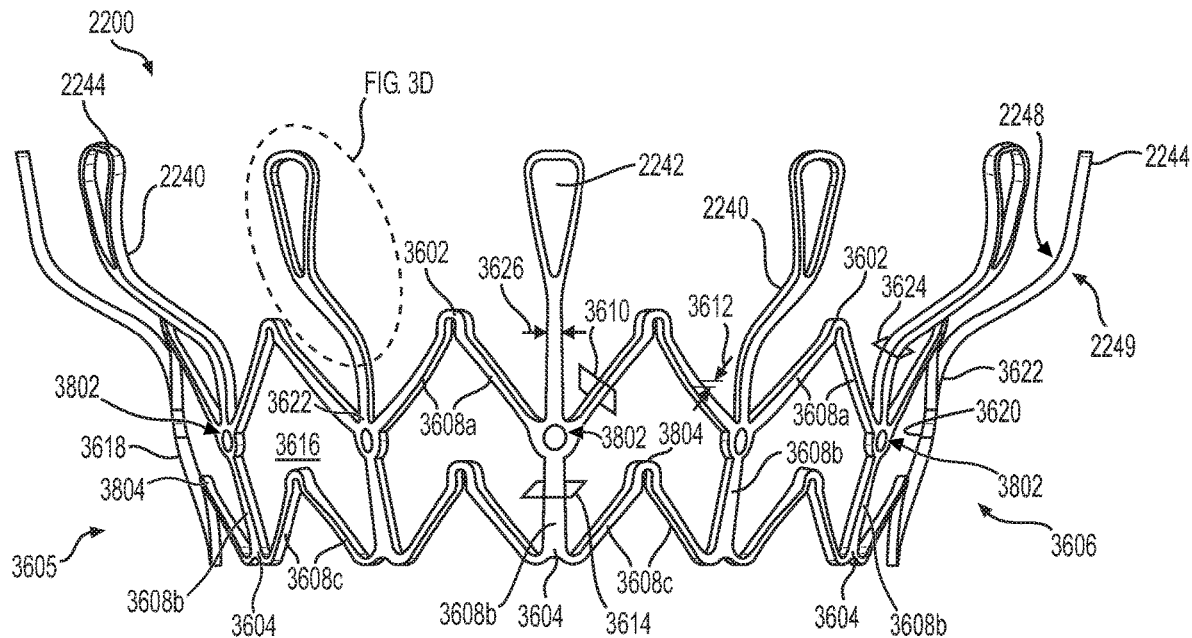
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
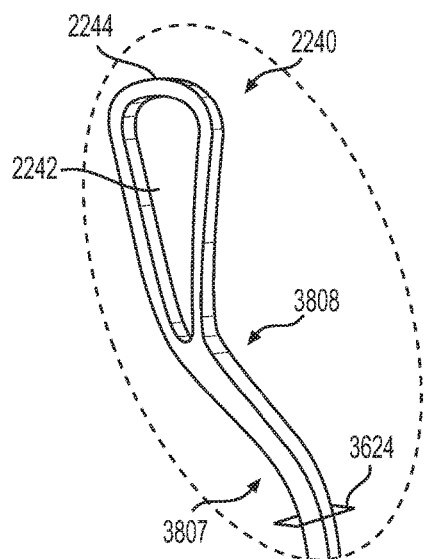
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

Figure 4B:
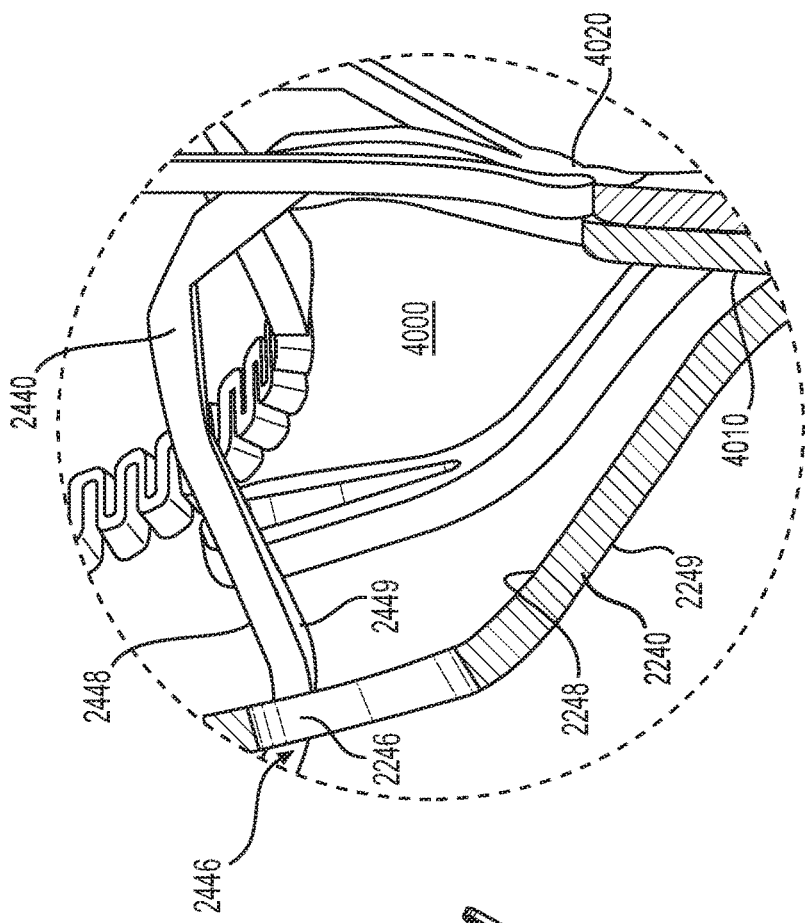
FIG. 4B illustrates an enlarged view of a volume between an atrial anchoring arm and a ventricular anchoring leg of the exemplary frame of FIG. 4A, consistent with various embodiments of the present disclosure.
Figure 4A:
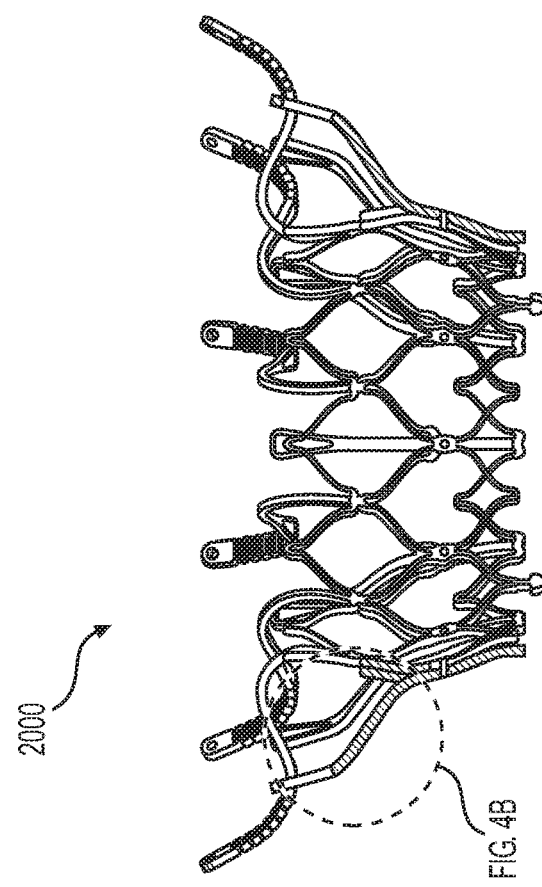
FIG. 4A illustrates a cross-sectional view of the exemplary frame of FIG. 2A, consistent with various embodiments of the present disclosure.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

Figures 5D, 5E:
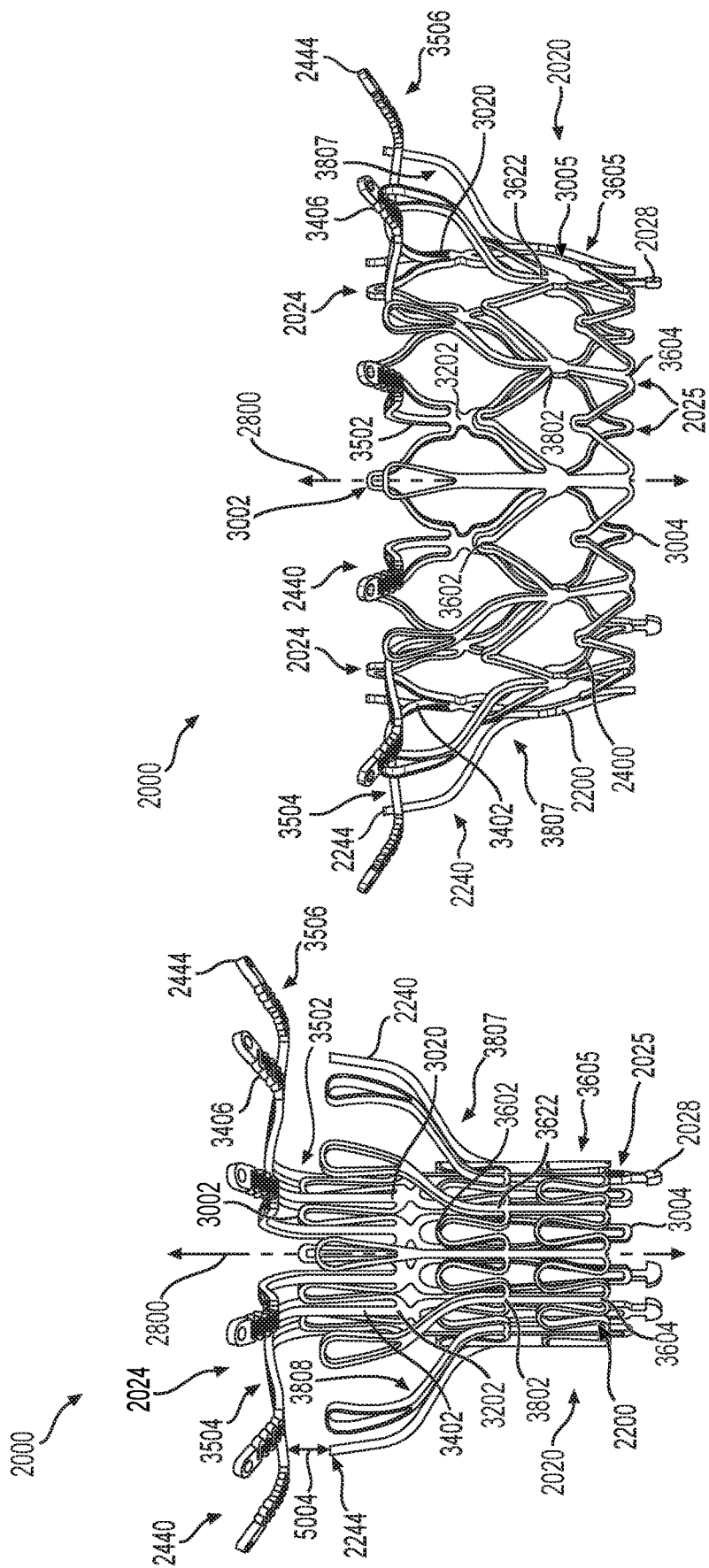

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
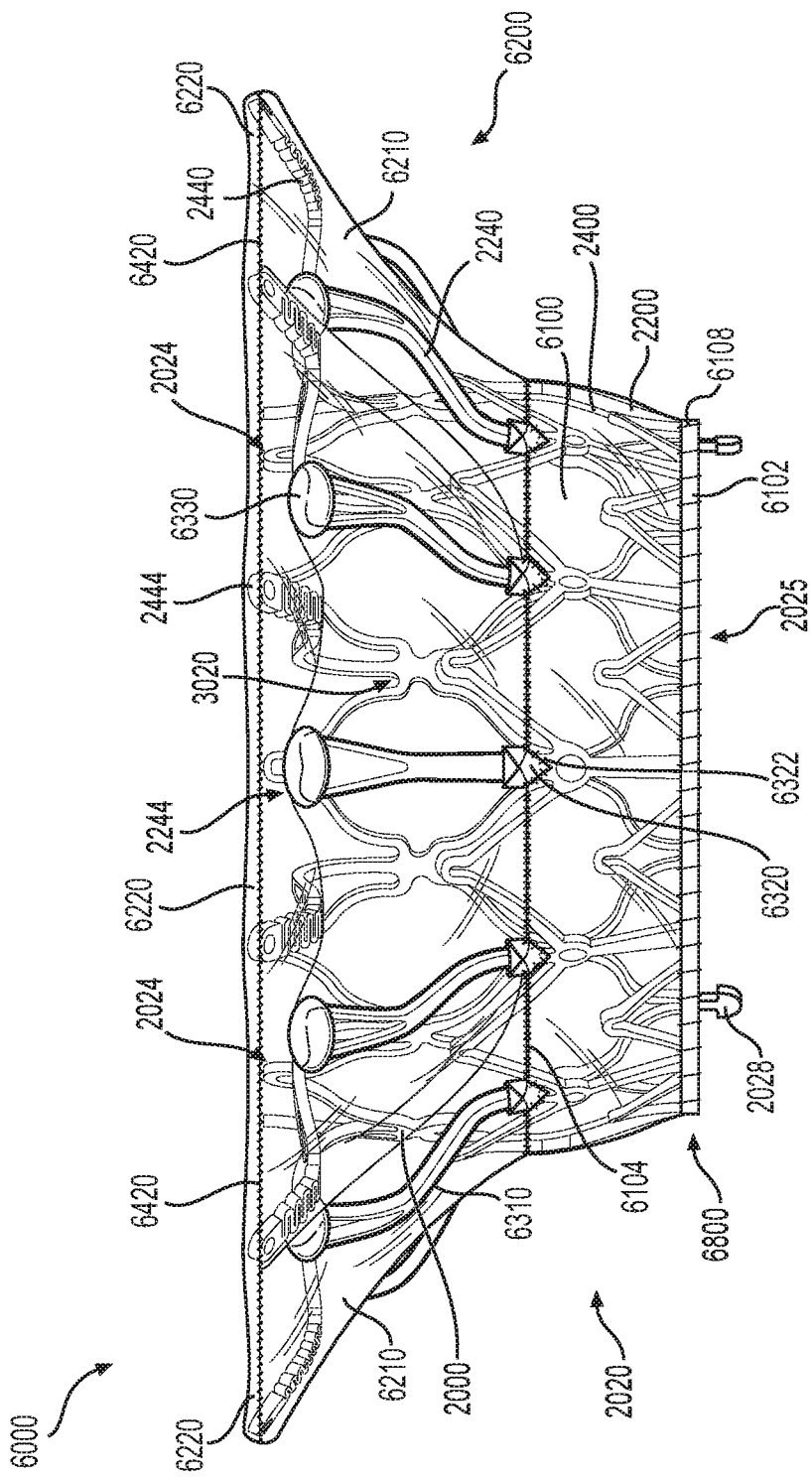
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
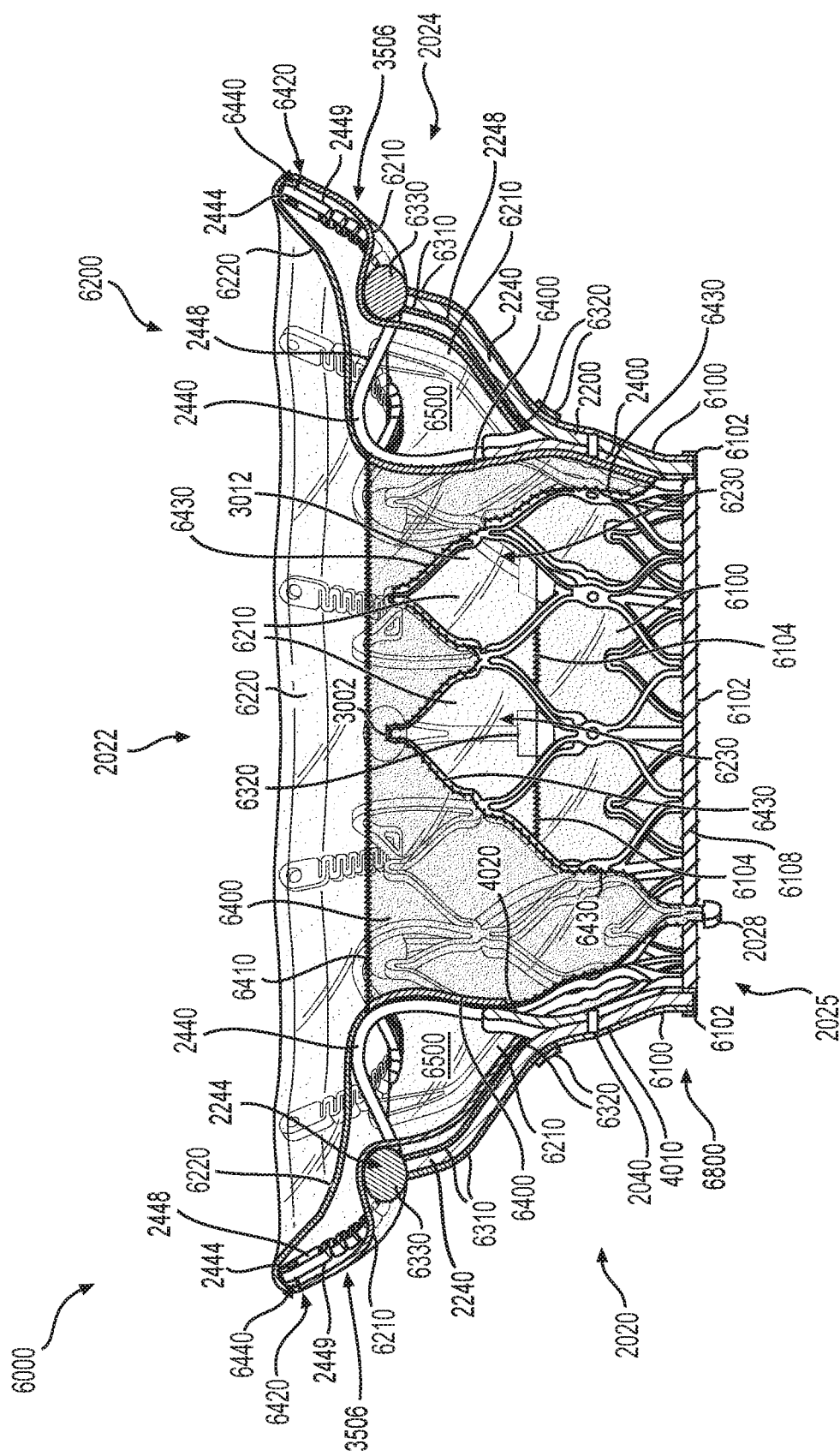
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
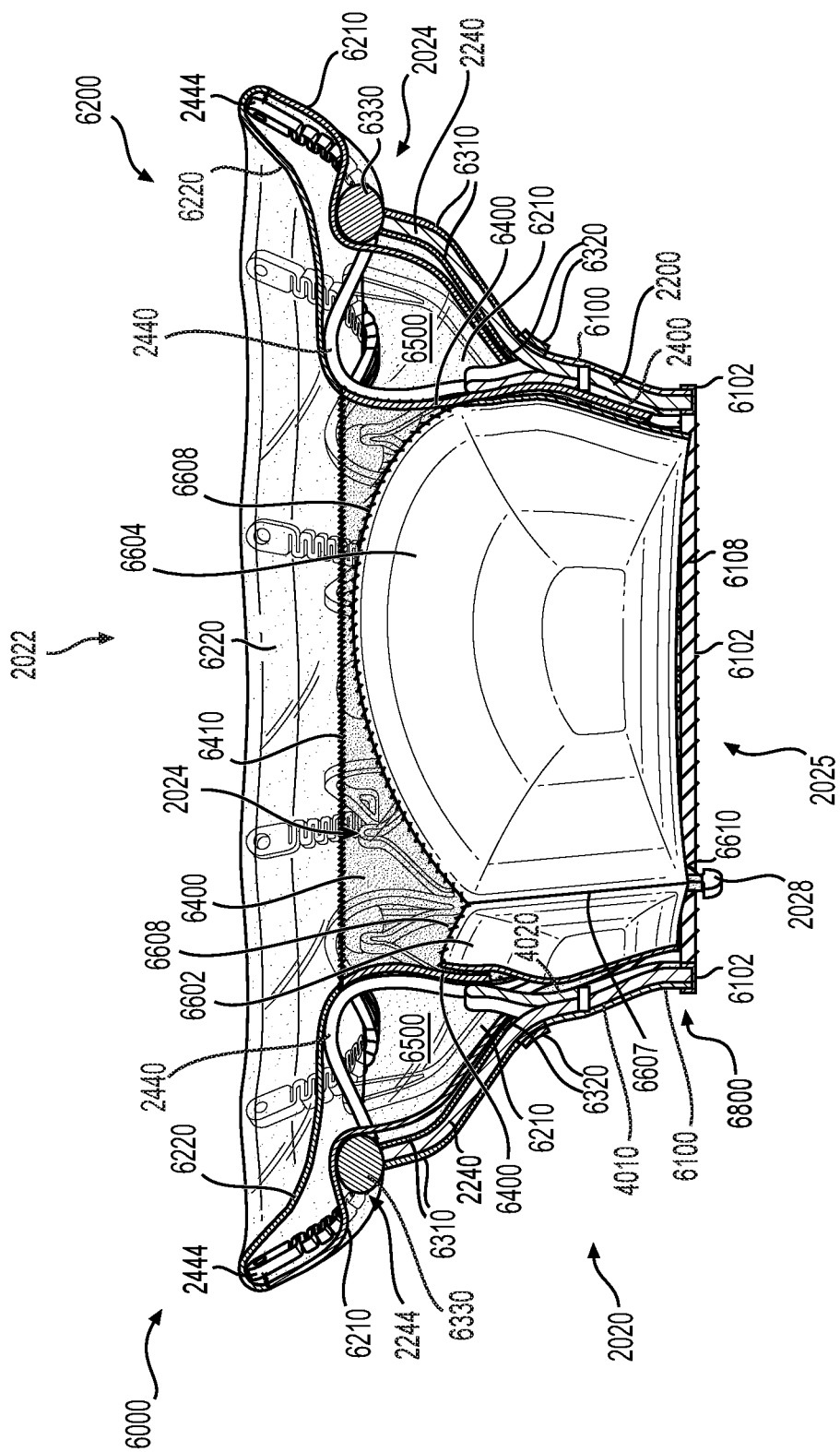
FIG. 6C illustrates a cross-sectional view of the exemplary prosthetic valve of FIG. 6A with leaflets, consistent with various embodiments of the present disclosure.

FIG. 6C illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
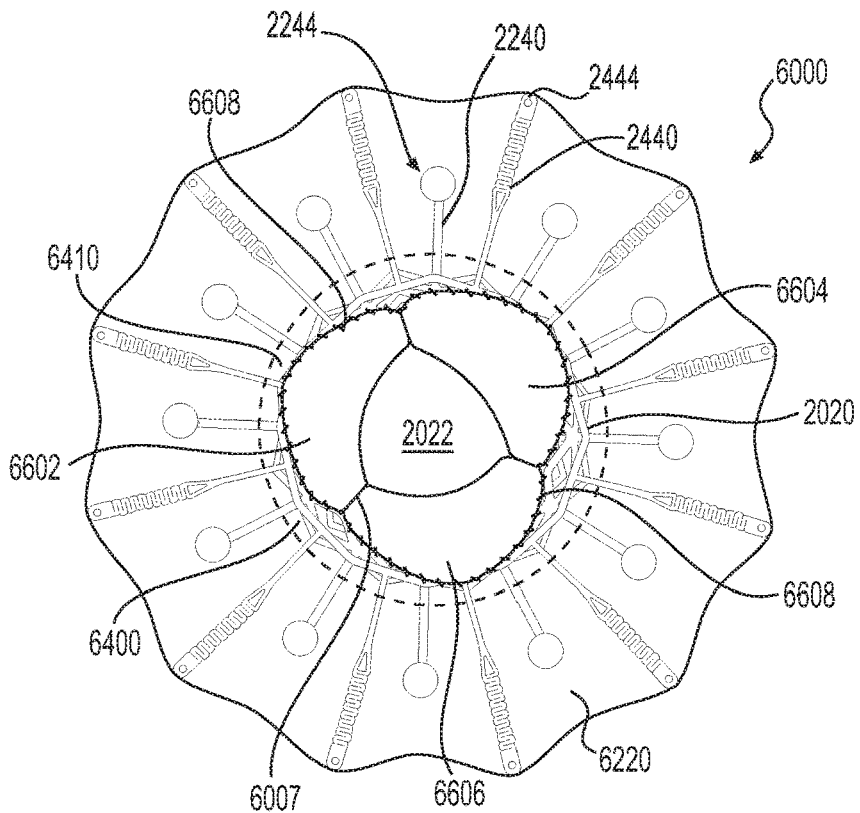
FIG. 6D illustrates a top plan view of the exemplary prosthetic valve of FIG. 6A with uninflated leaflets, consistent with various embodiments of the present disclosure.
Figure 6E:
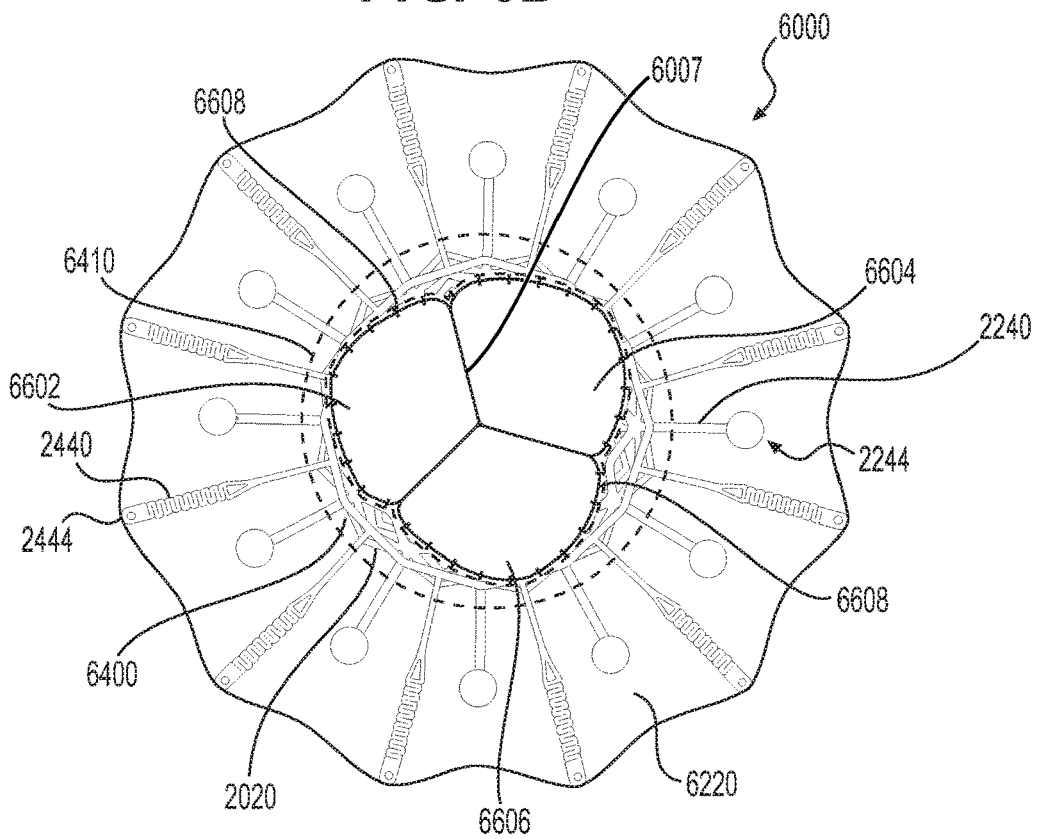
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
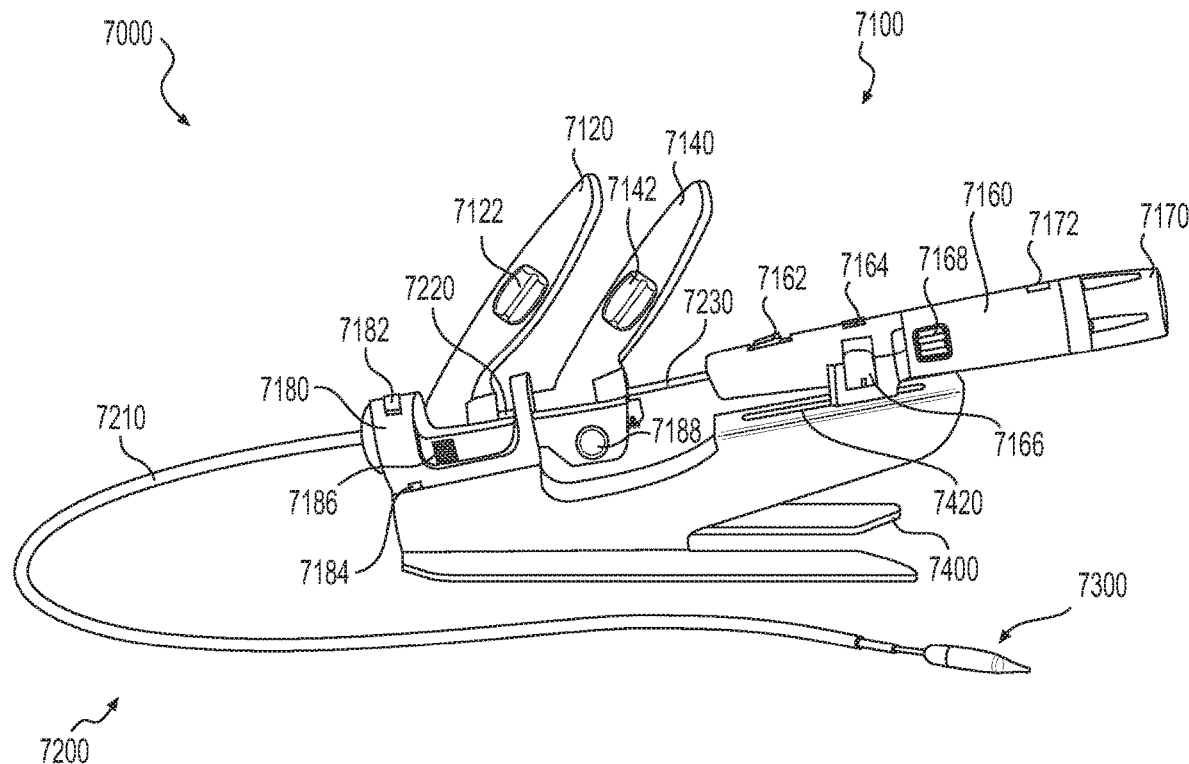
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
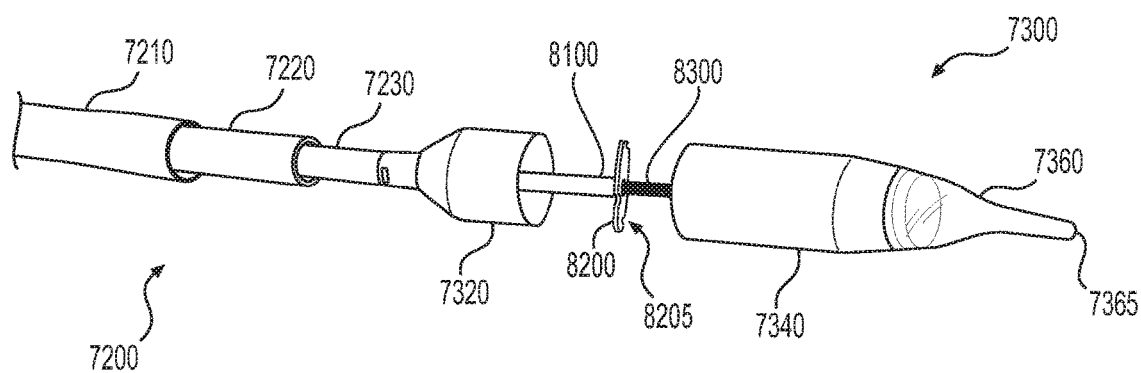
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

Figure 7D:
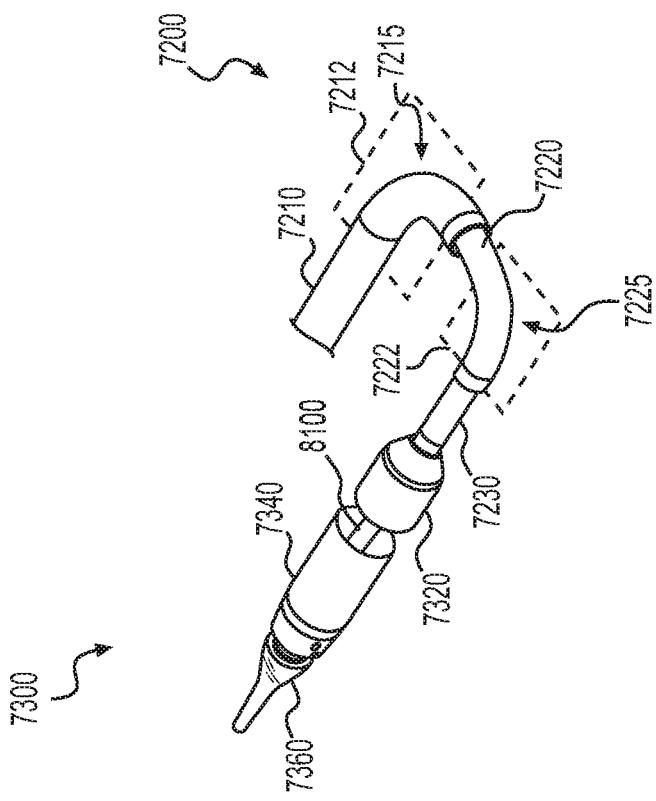
FIG. 7D illustrates another exemplary configuration of the telescoping catheter assembly and delivery capsule of FIG. 7C, consistent with various embodiments of the present disclosure.
Figure 7C:
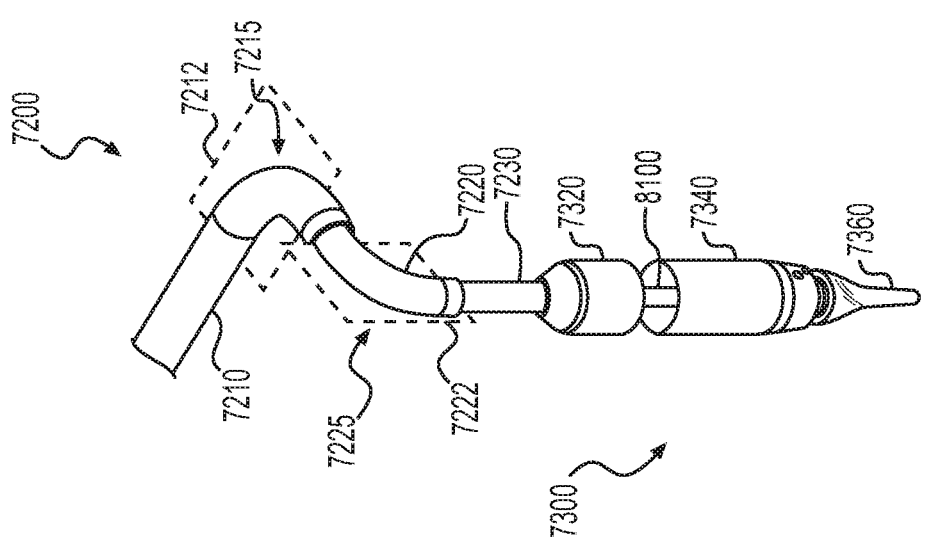
FIG. 7C illustrates an exemplary configuration of a telescoping catheter assembly and the delivery capsule of the exemplary prosthetic valve delivery system of FIG. 7A, consistent with various embodiments of the present disclosure.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
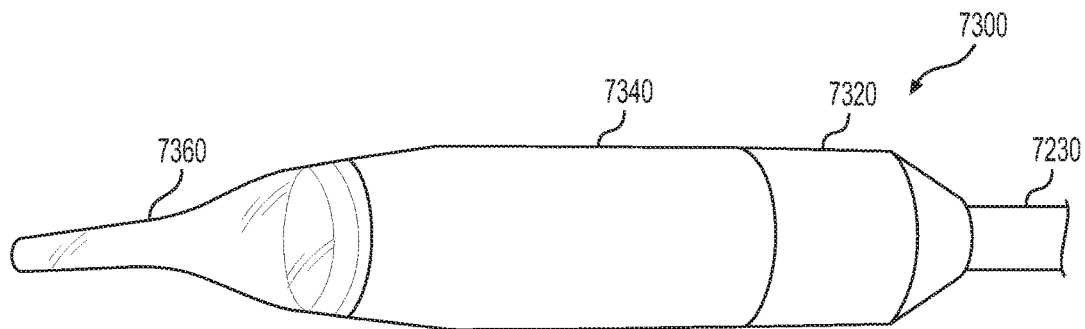
FIG. 8A illustrates another enlarged view of the exemplary delivery capsule of the prosthetic valve delivery system of FIG. 7A in a closed configuration, consistent with various embodiments of the present disclosure.
Figure 8B:
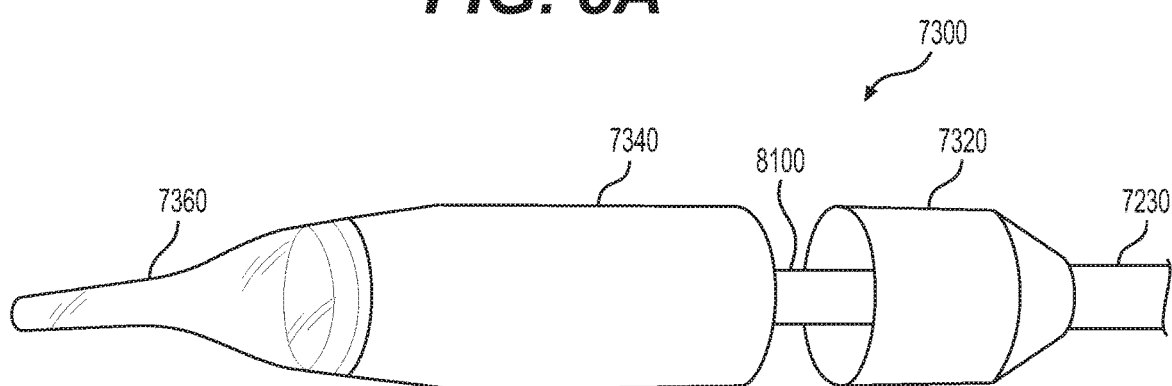
FIG. 8B illustrates the exemplary delivery capsule of FIG. 8A in an open configuration, consistent with various embodiments of the present disclosure.
Figure 8C:
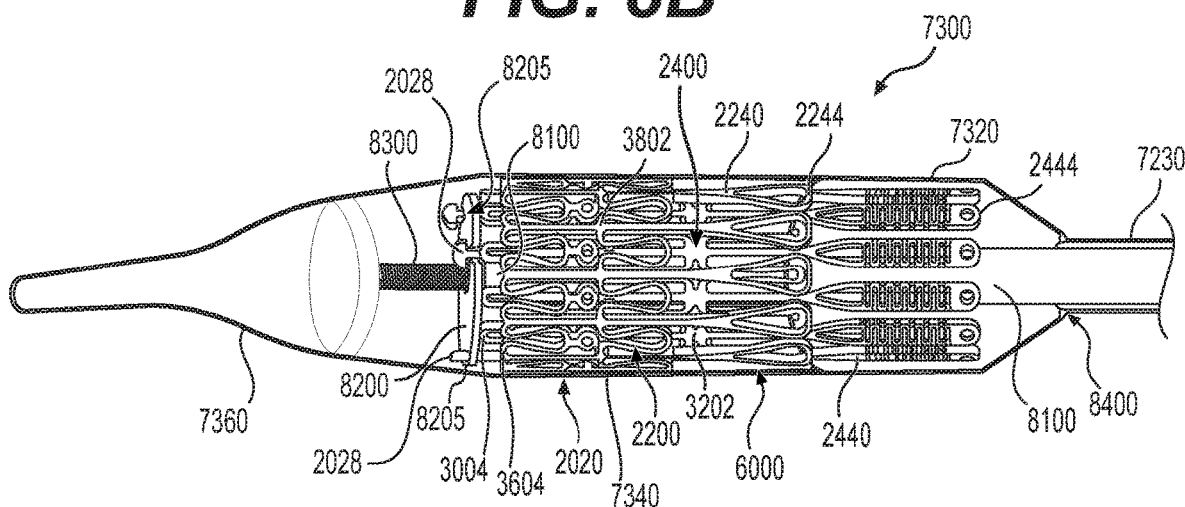
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
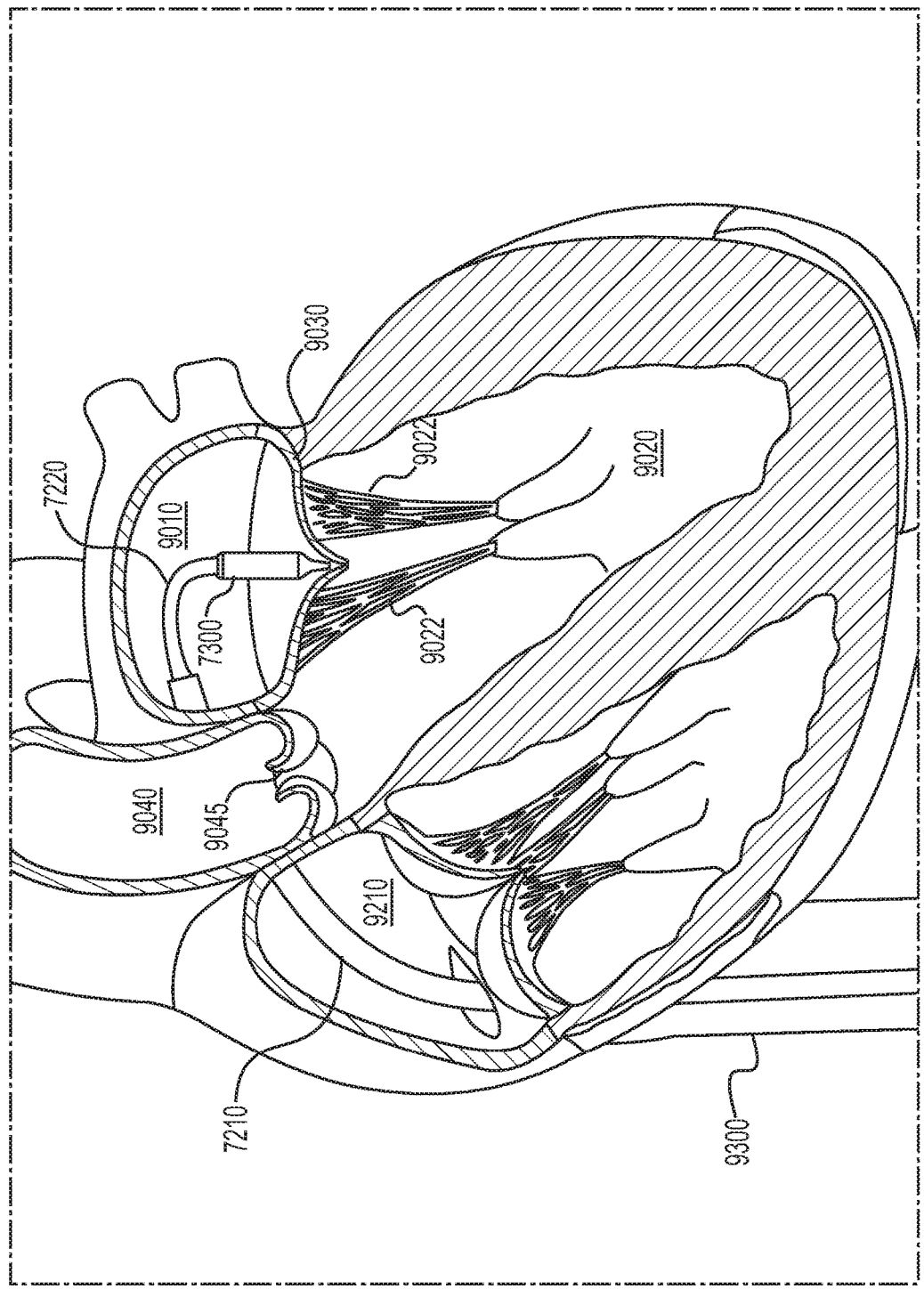
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10A:
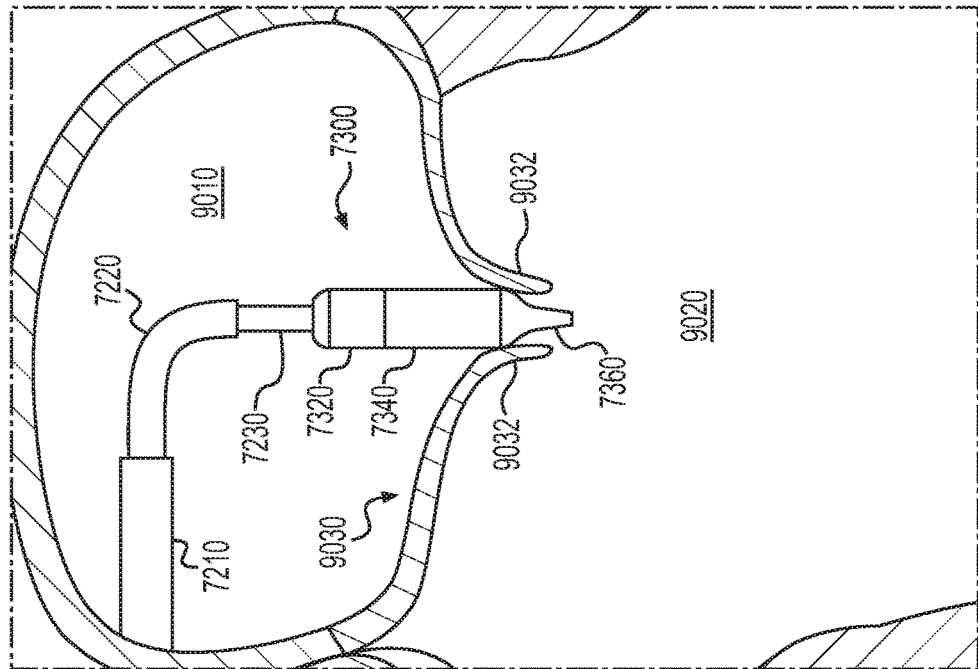
FIGS. 10A-10H depict implantation of the prosthetic valve of FIGS. 6A-6E within a native mitral valve by the exemplary prosthetic valve delivery system of FIG. 7A, consistent with various embodiments of the present disclosure.
Figure 10B:
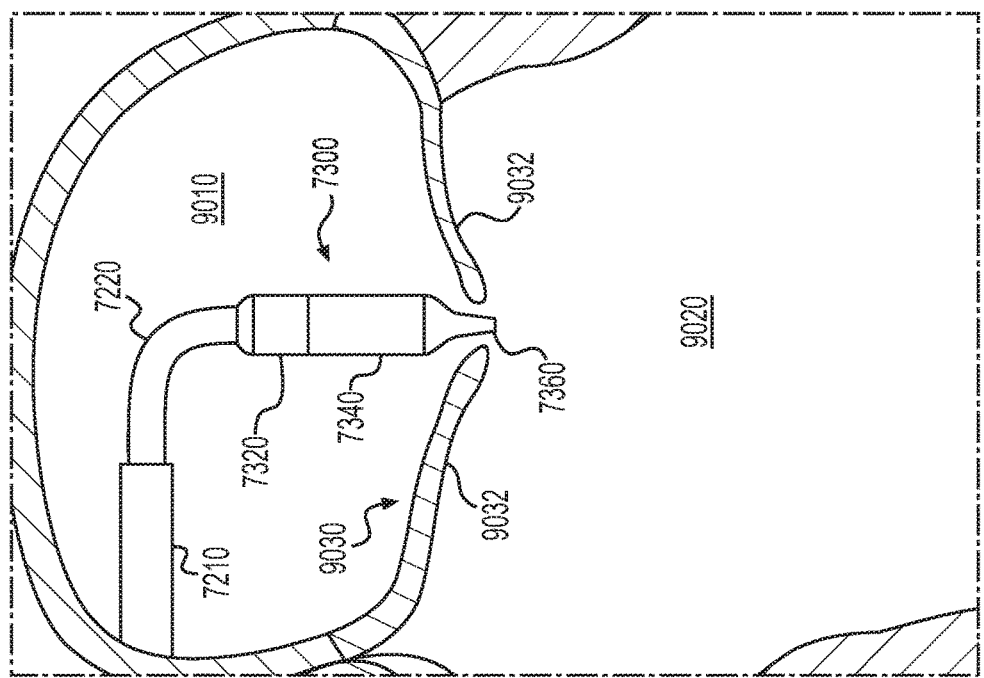
Figure 10D:
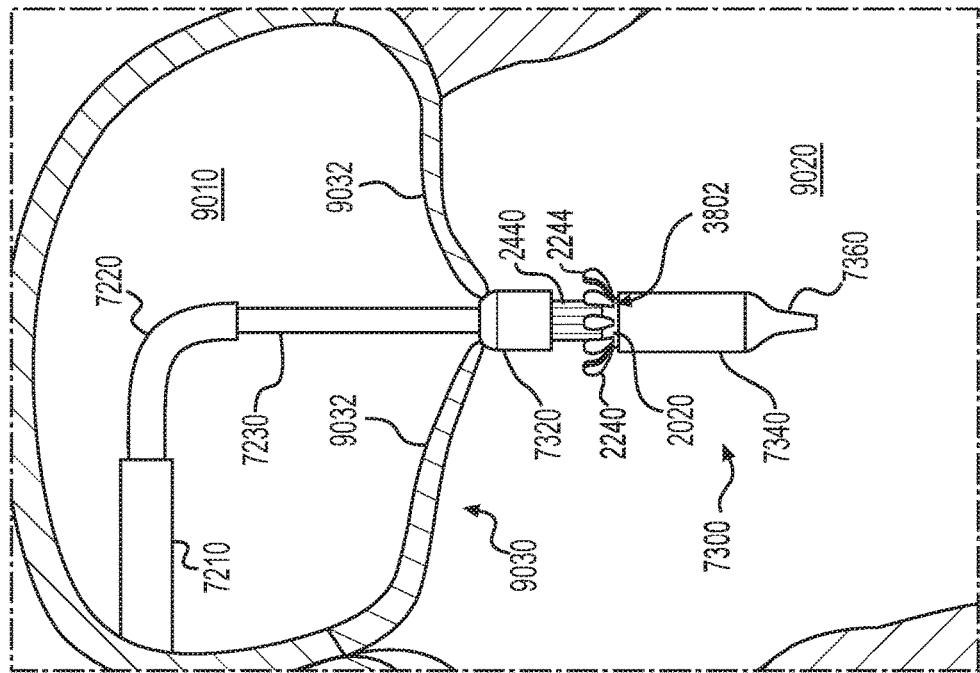
Figure 10C:
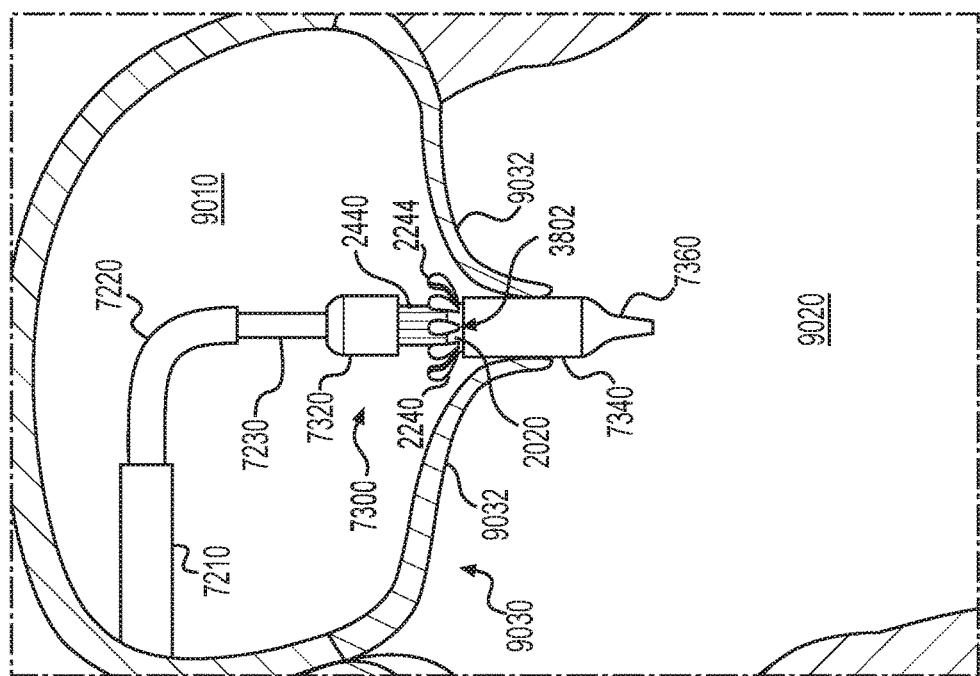

FIGS. 10A-10H depict an exemplary implantation method of prosthetic valve 6000 within a mitral valve 9030. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
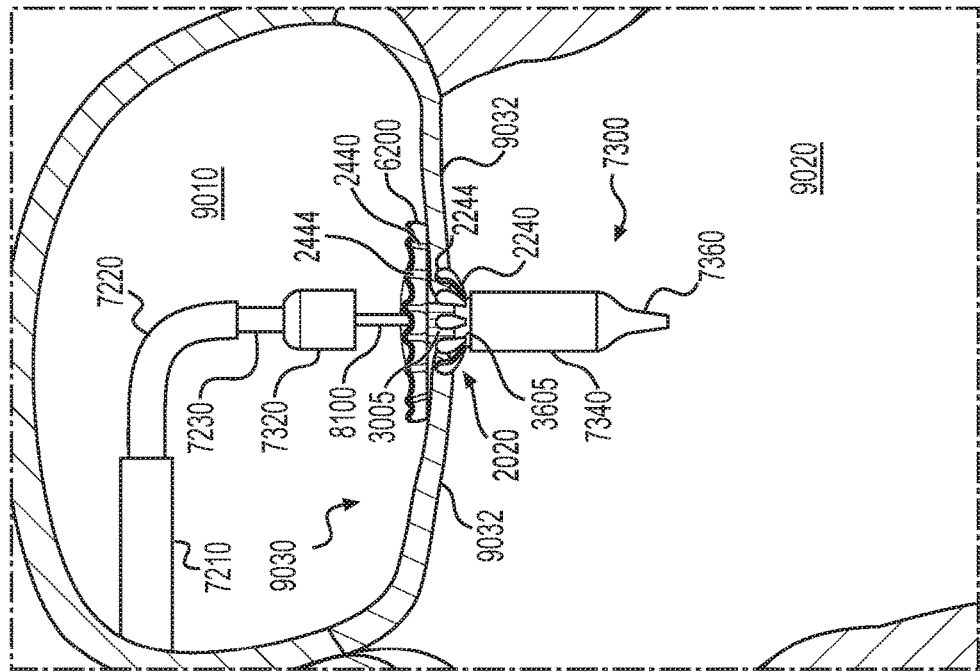
Figure 10E:
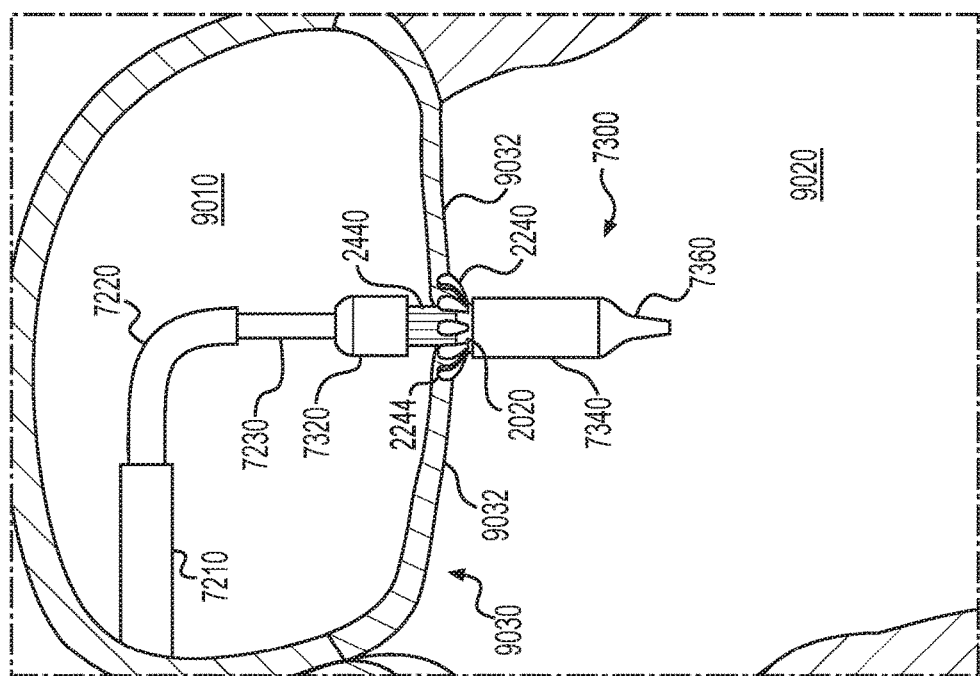

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

Figure 10G:
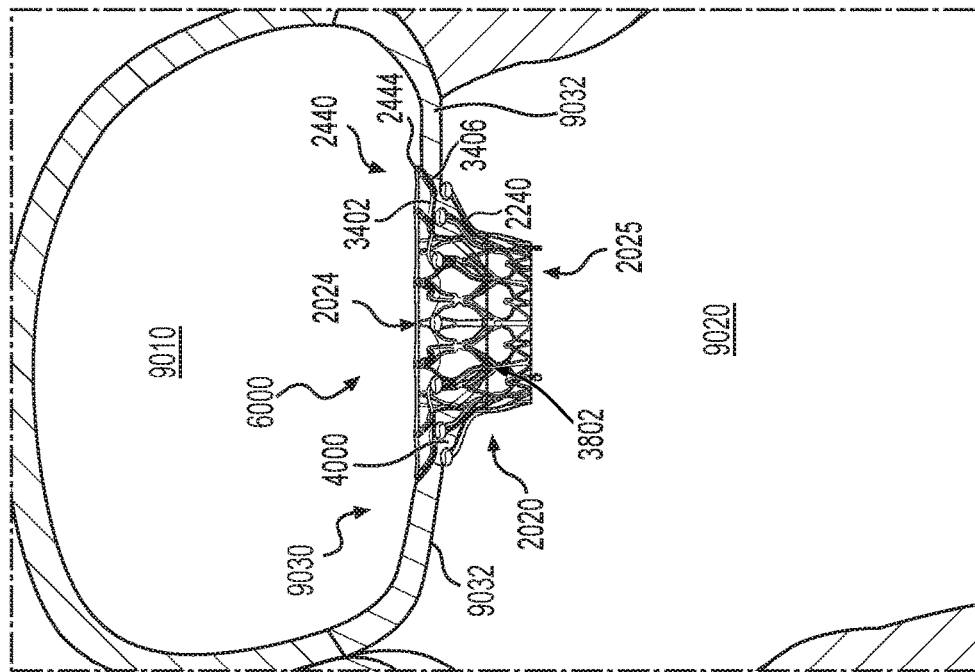
Figure 10H:
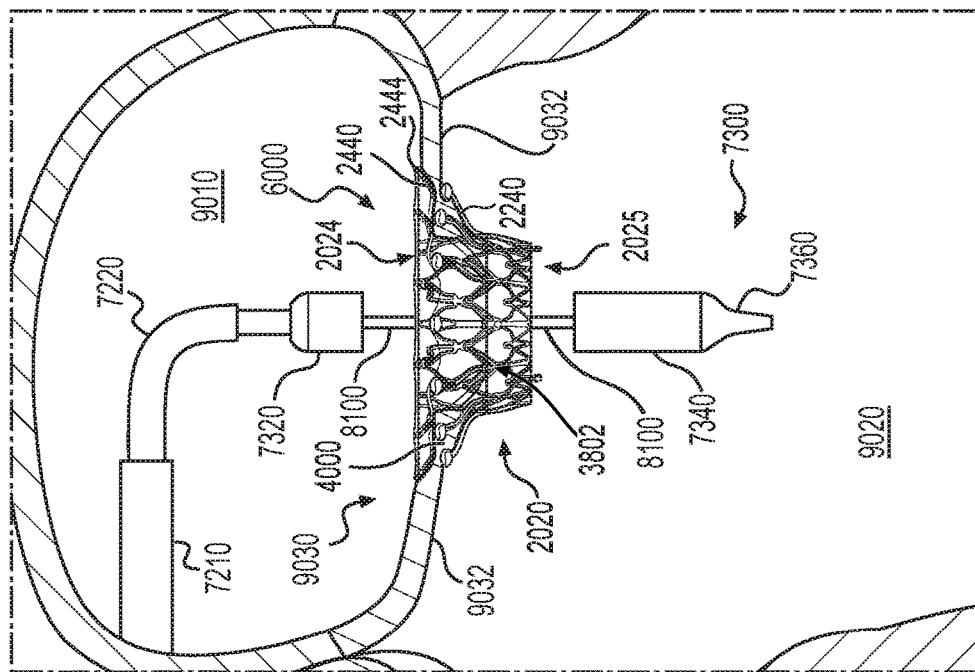

In FIG. 10G, the distal capsule portion 7340 may be advanced further until the annular valve body 2020 is released from the capsule and allowed to radially expand. Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments of the present disclosure relate to prosthetic valves, including prosthetic heart valves. While the present disclosure provides examples of prosthetic heart valves, and in particular prosthetic mitral valves, it should be noted that aspects of the disclosure in their broadest sense are not limited to a prosthetic heart valve. Rather, the foregoing principles may be applied to other prosthetic valves as well. Prosthetic heart valve 6000, illustrated in FIGS. 6A-6E, is one example of a prosthetic valve in accordance with the present disclosure.

In some embodiments, an exemplary prosthetic valve may be configuration for implantation within a native atrioventricular valve and may regulate blood flow between the atrium and ventricle. For example, prosthetic heart valve 6000 illustrated in FIGS. 6A-6C may include a fluid-impervious cuff 6200 configured to extend from an inner lumen 2022 of the prosthetic valve to terminal arm ends 2444 of a plurality of atrial anchoring arms 2440. Because cuff 6200 is constructed of a fluid-impervious material, cuff 6200 may be configured to minimize or block flow of blood and other fluids through any portion of the prosthetic valve 6000 except for lumen 2022. In addition, atrial anchoring arms 2440 of the prosthetic valve (including terminal arm ends 2444) may be configured to contact and, in some embodiments, press against atrial tissue of a native heart valve. This is illustrated in FIGS. 10G-10H, which depict atrial anchoring arms 2440 of prosthetic valve 6000 arranged in contact with, and exerting a ventricularly-directed force (that is, a force directed downwards towards ventricle 9020) upon, atrial tissue of native mitral valve 9030. As a result, cuff 6200 of prosthetic valve 6000 may also be configured to minimize or block passage of blood and other fluids between the prosthetic valve 6000 (including terminal arm ends 2444) and native valve tissue, a condition known as perivalvular leakage. As a result, prosthetic valve 6000 may be configured to prohibit passage of blood and other fluids between atrium 9010 and ventricle 9020, except by passage through inner lumen 2022, in which leaflets 6602, 6604, and 6606 may be situated.

In some embodiments, an exemplary prosthetic valve may be expandable, such as between a radially-contracted configuration (e.g., a crimped state) and a radially-expanded configuration. For example, FIG. 5A illustrates a radially-contracted configuration of an exemplary prosthetic valve, and FIG. 5E illustrates a radially-expanded configuration of the exemplary prosthetic valve. The diameter of the prosthetic valve, including annular valve body 2020, ventricular anchoring legs 2240, and atrial anchoring arms 2440, may be reduced when the prosthetic valve assumes the radially-contracted configuration, as illustrated in FIG. 5A. The diameter of the prosthetic valve may be increased when the prosthetic valve assumes the radially-expanded configuration, as illustrated in FIG. 5E. For example, an annular valve body 2020 of the prosthetic valve may radially expand when the prosthetic valve assumes the radially-expanded configuration. Additionally, or alternatively, a plurality of ventricular anchoring legs 2240 and/or atrial anchoring arms 2440 may be configured to deflect radially outward from the exemplary annular valve body 2020 when the prosthetic valve assumes the radially-expanded configuration.

In some embodiments, the exemplary prosthetic valve may be configured to be radially contracted into a radially-contracted configuration for introduction to an implantation site, such as on or within a delivery device. Accordingly, in some embodiments, the radially-contracted configuration may also be a delivery configuration, in which the prosthetic valve is arranged for delivery to the implantation site. Once at or near the implantation site, the prosthetic valve may be radially expanded to a radially-expanded configuration, in which the prosthetic valve may be anchored at the implantation site. Accordingly, in some embodiments, the radially-expanded configuration may also be a deployed configuration, in which the prosthetic valve is released from the delivery tool and seated at the implantation site.

In some embodiments, an exemplary prosthetic valve may be configured for self-expansion to the radially-expanded configuration; that is, the prosthetic valve may be biased to assume the radially-expanded configuration due to, at least in part, the design and/or material composition of the prosthetic valve. The self-expanding prosthetic valve may be constructed of a shape memory material such as nickel titanium alloy (Nitinol), which may permit the prosthetic valve to expand to a pre-determined diameter upon removal of a constraining force and/or application of heat or energy. For example, the prosthetic valve may be contracted and held in the radially-contracted configuration by a constraining device, such as a sheath, catheter, stent, or delivery capsule. An example of such a constraining device is illustrated in FIG. 8C, which illustrates prosthetic heart valve 6000 held in a radially-contracted configuration within delivery capsule 7300. When the prosthetic valve is positioned at or near the implantation site, the constraining force may be removed and the prosthetic valve allowed to self-expand to the radially-expanded configuration. Additionally, or alternatively, an exemplary prosthetic valve may be configured to expand due to application of radially expansive forces thereupon. For example, the prosthetic valve may be placed, in its radially-contracted configuration, upon an expansion device such as a balloon catheter. Upon positioning at the implantation site, the expansion device may exert an outwardly-directed force upon the prosthetic valve, causing it to expand to the radially-expanded configuration.

In some embodiments, the exemplary prosthetic valve may be configured for implantation at a treatment site within the body, such as within or adjacent to a native heart valve structure. In some embodiments, a prosthetic valve may be configured for transcatheter delivery to the implantation site via a variety of approaches, such as transapically, transatrially, and/or transseptally. In some embodiments, the prosthetic valve may be configured for implantation in the annulus or orifice of a native heart valve structure (e.g., a native heart valve). For example, in FIGS. 10A-10H, prosthetic valve 6000 may be delivered to and expanded within native mitral valve 9030 such that prosthetic valve 6000 is anchored within native mitral valve 9030. In some embodiments, the exemplary prosthetic valve may be configured to grasp tissue of the native heart valve to more firmly anchor the prosthetic valve within the native heart valve. For example, an exemplary prosthetic valve may be configured to grasp the native leaflets and/or native heart valve annulus to firmly seat the prosthetic valve within the valve annulus, thus preventing the prosthetic valve from migrating or dislodging from within the native heart valve annulus.

In some embodiments, the exemplary prosthetic valve may include an annular valve body. The annular valve body may be configured to receive or otherwise support a flow control device, such as one or more leaflets, for regulating flow of blood or other bodily fluids through the prosthetic valve. For example, the flow control device (e.g., leaflets) may be secured directly to the annular valve body and/or to an intermediate structure that is in turn secured to the valve body. As a result, when the prosthetic valve is implanted within a native mitral valve, the flow control device (e.g., leaflets) may regulate fluid passage through the native mitral valve, thus restoring and/or replacing the functionality of the mitral valve. For example, FIGS. 6D and 6E illustrate an exemplary prosthetic heart valve 6000 including an annular valve body 2020 with prosthetic leaflets 6602, 6604, and 6606 received within the annular valve body. In the example of a prosthetic mitral valve, the flow control device of the annular valve body may be configured to permit flow of blood and other fluids in one direction (e.g., from the left atrium to the left ventricle) and to prevent flow of blood and other fluids in a second, opposite direction (e.g., from the left ventricle to the left atrium).

In some embodiments, the valve body may be annular or ring-shaped, and may include a tubular annulus or opening extending longitudinally through the valve body. In some embodiments, the tubular annulus or opening may extend longitudinally along the entire axial length of the annular valve body. For example, FIG. 2B illustrates an exemplary frame 2000 of a prosthetic heart valve. Heart valve frame 2000 may include an annular valve body 2020 having a tubular axial lumen 2022 extending longitudinally along the entire length of annular valve body 2020; accordingly, lumen 2022 may be considered a tubular annulus in some embodiments. In some embodiments, the annulus of the valve body may be tubular because the annulus may be circular, elliptical, or oval-shaped and may extend longitudinally along the entire axial length of the annular valve body. In some embodiments, the annular valve body may be sized and configured to be seated within the orifice of a native heart valve. For example, as depicted in FIG. 10H, annular valve body 2020 may be situated within the orifice of mitral valve 9030, specifically between native leaflets 9032. In some embodiments, the annular valve body may be configured to have a smaller diameter, when fully-expanded, than the diameter of the orifice of the native heart valve. In such embodiments, the annular valve body may be anchored in the native heart valve by anchoring structures, such as one or more atrial anchoring arms and/or one or more ventricular anchoring legs. Alternatively, the annular valve body may be configured to expand to an equal or greater diameter than the diameter of the heart valve orifice such that the annular valve body is anchored within the heart valve.

The annular valve body may have a circular, oval-shaped, elliptical, or D-shaped cross-section and may be symmetrical about at least one axis of the annular valve body. For example, FIG. 2B illustrates exemplary annular valve body 2020, which may have a substantially circular cross-section and which may be symmetrical about the longitudinal axis of the prosthetic valve. Alternatively, the annular valve body may have any suitable cross-sectional shape, with at least one tubular annulus within the annular valve body. In some embodiments, at least a portion of the annular valve body may be cylindrical, with a substantially constant diameter along the entire longitudinal length of the annular valve body. Alternatively, the annular valve body may have a variable diameter at different portions of the annular valve body (e.g., at different longitudinal portions of the annular valve body). For example, exemplary annular valve body 2020 illustrated in FIGS. 2A and 2D may have a diameter at a longitudinally central portion of the valve body (that is, in a middle portion of the annular valve body relative to longitudinal axis 2800) that may be larger than the diameter of the annular valve body 2020 at the atrial end 2024 of the annular valve body (i.e., the top of annular valve body 2020 in FIG. 2A) and/or the diameter of the annular valve body 2020 at the ventricular end 2025 of the annular valve body (i.e., the bottom of annular valve body 2020 in FIG. 2A). Advantageously, such a configuration may improve the seating of the annular valve body within the mitral valve orifice, providing an improved pressure fit therebetween.

In some embodiments, the annular valve body may be configured to radially expand independently of other components of the exemplary prosthetic valve. For example, the annular valve body may be configured to remain in a radially-contracted configuration while other components of the prosthetic valve, such as one or more tissue anchors, are deployed radially outward. For example, FIG. 5B depicts an exemplary annular valve body 2020 arranged in a radially-contracted configuration while a plurality of ventricular anchoring legs 2240, and in particular the terminal leg ends 2244 of the ventricular anchoring legs 2240, are deployed radially outward (e.g., due to removal of a constraining delivery device from the ventricular anchoring legs). In the configuration illustrated in FIG. 5B, the heart valve frame 2000 may additionally include a plurality of atrial anchoring arms 2440 configured in a radially-contracted configuration. Similarly, FIG. 5C depicts an exemplary configuration in which the annular valve body 2020 and a plurality of ventricular anchoring legs 2240 may be arranged in a radially-contracted configuration, while a plurality of atrial anchoring arms 2440, and in particular the terminal arm ends 2444 of the atrial anchoring arms 2440, are deployed radially outward (e.g., due to removal of a constraining delivery device from the atrial anchoring arms). Further, FIG. 5D depicts an exemplary configuration in which the annular valve body 2020 may be arranged in a radially-contracted configuration, while the plurality of atrial anchoring arms 2440 and the plurality of ventricular anchoring legs 2240 are deployed radially outward.

In some embodiments, the exemplary prosthetic valve may include a plurality (that is, one or more) of atrial anchoring arms configured to extend radially outward from the annular valve body. For example, FIG. 2A illustrates an annular valve body 2020 and a plurality of atrial anchoring arms 2440 extending radially outward from the annular valve body. The atrial anchoring arms may be configured to anchor the prosthetic valve at an implantation site, such as within or near a native heart valve. For example, the atrial anchoring arms may be configured to engage atrial tissue of a native mitral valve to anchor the prosthetic valve within the mitral valve. In some embodiments, the atrial anchoring arms may be configured to be positioned at least partially within an atrium upon implantation of the prosthetic valve within or near a native mitral valve, and to engage atrial tissue of the mitral valve. For example, FIGS. 10F-10H depict atrial anchoring arms 2440 of an exemplary prosthetic heart valve 6000. Atrial anchoring arms 2440 are situated within atrium 9010 and may engage the atrial side of native mitral valve 9030 to secure prosthetic heart valve 6000 within the mitral valve.

The prosthetic valve may include one atrial anchoring arm, two atrial anchoring arms, three atrial anchoring arms, four atrial anchoring arms, five atrial anchoring arms, six atrial anchoring arms, seven atrial anchoring arms, eight atrial anchoring arms, nine atrial anchoring arms, ten atrial anchoring arms, eleven atrial anchoring arms, twelve atrial anchoring arms, thirteen atrial anchoring arms, fourteen atrial anchoring arms, fifteen atrial anchoring arms, sixteen atrial anchoring arms, seventeen atrial anchoring arms, eighteen atrial anchoring arms, nineteen atrial anchoring arms, twenty atrial anchoring arms, or any other suitable number of atrial anchoring arms. For example, exemplary prosthetic valve 6000 depicted in FIG. 2B includes twelve atrial anchoring arms 2440.

In some embodiments, the atrial anchoring arms may be configured to extend radially outward from the annular valve body. In some embodiments, the term "radially outward" may refer to a direction extending away from the center of the annular valve body (for example, away from the longitudinal axis of the exemplary prosthetic valve). In some embodiments, the atrial anchoring arms may be connected to the annular valve body and configured to extend radially outward from the annular valve body. For example, in FIGS. 5D and 5E, atrial anchoring arms 2440 may be connected to annular valve body 2020 at arm attachment junctions 3202 and may extend radially outward from the annular valve body 2020. In some embodiments, the atrial anchoring arms may be physically connected to the annular valve body, such as by welding or adhesive. In some alternative embodiments, the atrial anchoring arms may be integrally formed with the annular valve body. In some further alternative embodiments, the atrial anchoring arms may not be secured directly to the annular valve body; however, the atrial anchoring arms may be configured to extend in a radially outward direction from the annular valve body.

In some embodiments, the locations of connection between the atrial anchoring arms and annular valve body may be spaced at a regular interval about a circumference of the annular valve body. For example, in FIG. 2A, the atrial anchoring arms 2440 may extend from the annular valve body 2020 at arm attachment junctions 3202. Arm attachment junctions 3202 may be spaced at a regular interval about the circumference of annular valve body 2020. Additionally, or alternatively, the locations of connection between the atrial anchoring arms and annular valve body may be arranged along a plane perpendicular to the longitudinal axis of the prosthetic valve. For example, in FIG. 2A, the arm attachment junctions 3202 may be arranged along a plane perpendicular to longitudinal axis 2800. That is, the arm attachment junctions 3202 may be situated at the same axial position along longitudinal axis 2800.

In some embodiments, each atrial anchoring arm may include a proximal arm end connected to or otherwise secured relative to the annular valve body, and a terminal arm end configured to extend radially outward from the annular valve body and, thus, from the proximal arm end of the atrial anchoring arm. In various embodiments, the term "proximal" refers to a portion of a feature (e.g., an atrial anchoring arm) situated in closest proximity to the annular valve body and may, in some embodiments, include a point of connection between the feature (e.g., the atrial anchoring arm) and the annular valve body. In various embodiments, the term "terminal" refers to a portion of a feature (e.g., an atrial anchoring arm) furthest from the point of connection between that feature and the annular valve body. For example, atrial anchoring arms 2440 illustrated in FIGS. 2A and 3A may include a proximal arm end 3020 connected to annular valve body 2020 (e.g., at arm attachment junction 3202) and a terminal arm end 2444 configured to extend radially outward from the annular valve body 2020 and from the proximal arm end 3020.

In some embodiments, each of the plurality of atrial anchoring arms may include a native valve tissue engaging portion. The native valve tissue engaging portion at the atrial anchoring arms may include at least a portion of a surface of each atrial anchoring arm configured to contact native valve tissue when the prosthetic valve is implanted. For example, in FIG. 3A, ventricularly-facing arm surface 2449 may constitute the native valve tissue engaging portion, since surface 2449 may be configured to contact atrial tissue of a native mitral valve when the prosthetic valve is implanted in the native mitral valve. In some embodiments, the entire surface 2449 may constitute the native valve tissue engaging portion of each atrial anchoring arm. In some alternative embodiments, a portion of surface 2449, including the sections of surface 2449 extending through intermediate arm portion 3504 and distal arm portion 3506 (illustrated in FIG. 3B), may constitute the native valve tissue engaging portion of each atrial anchoring arm.

In some embodiments, the exemplary prosthetic valve may include a plurality (that is, one or more) of ventricular anchoring legs configured to extend radially outward from the annular valve body. For example, FIG. 2A illustrates an annular valve body 2020 and a plurality of ventricular anchoring legs 2240 extending radially outward from the annular valve body. The ventricular anchoring legs may be configured to anchor the prosthetic valve at an implantation site, such as within or near a native heart valve. For example, the ventricular anchoring legs may be configured to engage ventricular tissue of a native mitral valve to anchor the prosthetic valve within the mitral valve. In some embodiments, the ventricular anchoring legs may be configured to be positioned at least partially within a ventricle upon implantation of the prosthetic valve within or near a native mitral valve, and to engage ventricular tissue of the mitral valve. For example, FIGS. 10E-10H depict ventricular anchoring legs 2240 of an exemplary prosthetic heart valve 6000. Ventricular anchoring legs 2240 are situated within ventricle 9020 and may engage the ventricular side of native mitral valve 9030 to secure prosthetic heart valve 6000 within the mitral valve.

The prosthetic valve may include one ventricular anchoring leg, two ventricular anchoring legs, three ventricular anchoring legs, four ventricular anchoring legs, five ventricular anchoring legs, six ventricular anchoring legs, seven ventricular anchoring legs, eight ventricular anchoring legs, nine ventricular anchoring legs, ten ventricular anchoring legs, eleven ventricular anchoring legs, twelve ventricular anchoring legs, thirteen ventricular anchoring legs, fourteen ventricular anchoring legs, fifteen ventricular anchoring legs, sixteen ventricular anchoring legs, seventeen ventricular anchoring legs, eighteen ventricular anchoring legs, nineteen ventricular anchoring legs, twenty ventricular anchoring legs, or any other suitable number of ventricular anchoring legs. For example, exemplary prosthetic valve 6000 depicted in FIG. 2B includes twelve ventricular anchoring legs 2240.

In some embodiments, the ventricular anchoring legs may be configured to extend radially outward from the annular valve body. In some embodiments, the ventricular anchoring legs may be connected to the annular valve body and configured to extend radially outward from the annular valve body. For example, in FIGS. 5D and 5E, ventricular anchoring legs 2240 may be connected to annular valve body 2020 at leg attachment junctions 3802 and may extend radially outward from the annular valve body 2020. In some embodiments, the ventricular anchoring legs may be physically connected to the annular valve body, such as by welding or adhesive. In some alternative embodiments, the ventricular anchoring legs may be integrally formed with the annular valve body. In some further alternative embodiments, the ventricular anchoring legs may not be secured directly to the annular valve body; however, the ventricular anchoring legs may be configured to extend in a radially outward direction from the annular valve body.

In some embodiments, the locations of connection between the ventricular anchoring legs and annular valve body may be spaced at a regular interval about a circumference of the annular valve body. For example, in FIG. 2A, the ventricular anchoring legs 2240 may extend from the annular valve body 2020 at leg attachment junctions 3802. Leg attachment junctions 3802 may be spaced at a regular interval about the circumference of annular valve body 2020. Additionally, or alternatively, the locations of connection between the ventricular anchoring legs and annular valve body may be arranged along a plane perpendicular to the longitudinal axis of the prosthetic valve. For example, in FIG. 2A, the leg attachment junctions 3802 may be arranged along a plane perpendicular to longitudinal axis 2800. That is, the leg attachment junctions 3802 may be situated at the same axial position along longitudinal axis 2800.

In some embodiments, each ventricular anchoring leg may include a proximal leg end connected to or otherwise secured relative to the annular valve body, and a terminal leg end configured to extend radially outward from the annular valve body and, thus, from the proximal leg end of the ventricular anchoring leg. For example, ventricular anchoring legs 2240 illustrated in FIGS. 2A and 3C may include a proximal leg end 3622 connected to annular valve body 2020 (e.g., at leg attachment junction 3802) and a terminal leg end 2244 configured to extend radially outward from the annular valve body 2020 and from the proximal leg end 3622.

In some embodiments, each of the plurality of ventricular anchoring legs may include a native valve tissue engaging portion. The native valve tissue engaging portion of the ventricular anchoring legs may include at least a portion of a surface of each ventricular anchoring leg configured to contact native valve tissue when the prosthetic valve is implanted. For example, in FIG. 3C, inner leg surface 2248 may constitute the native valve tissue engaging portion, since surface 2248 may be configured to contact ventricular tissue of a native mitral valve when the prosthetic valve is implanted in the native mitral valve. In some embodiments, the entire surface 2248 may constitute the native valve tissue engaging portion of each ventricular anchoring leg. In some alternative embodiments, a portion of surface 2248, including the section of surface 2248 extending adjacent to distal leg opening 2242 (illustrated in FIG. 3D), may constitute the native valve tissue engaging portion of each ventricular anchoring leg.

In some embodiments, the atrial anchoring arms and ventricular anchoring legs may be configured to minimize or prevent migration of the prosthetic valve into an adjacent heart chamber after the prosthetic valve is implanted within or near a native heart valve. This may be due, at least in part, to the diameter of the atrial anchoring arms and/or the ventricular anchoring legs when they are radially-expanded. That is, the atrial anchoring arms and/or the ventricular anchoring legs may form a diameter, when in the radially-expanded configuration, which is larger than the diameter of the heart valve orifice; accordingly, the prosthetic valve may be prevented from axial migration (that is, migration towards the atrium or ventricle) due to the inability of the atrial anchoring arms and/or the ventricular anchoring legs to pass through the valve orifice. Additionally, or alternatively, the atrial anchoring arms and ventricular anchoring legs may be configured to grasp or clamp tissue of the native heart valve to further anchor the prosthetic valve in place. For example, in the embodiment of FIGS. 10G and 10H, atrial anchoring arms 2440 may clamp tissue by exerting a ventricularly-directed force (that is, a force directed downwards towards ventricle 9020 in FIGS. 10G and 10H) on the heart valve tissue. Similarly, ventricular anchoring legs 2240 may clamp the tissue by exerting an atrially-directed force (that is, a force directed upwards towards atrium 9010 in FIGS. 10G and 10H) on the heart valve tissue. These opposing forces may clamp or "sandwich" the heart valve tissue between the atrial anchoring arms and ventricular anchoring legs, thus firmly anchoring prosthetic heart valve 6000 within the native heart valve.

In some embodiments, the atrial anchoring arms and ventricular anchoring legs may be constructed of one or more materials, such as a polymer or metal. The one or more materials may be biocompatible and, in some embodiments, may have shape-memory and superelastic properties. For example, the atrial anchoring arms and ventricular anchoring legs may be constructed at least partially of Nitinol, stainless steel, chromium alloys, or another other suitable material. In some embodiments, the annular valve body, plurality of atrial anchoring arms, and plurality of ventricular anchoring legs may be constructed substantially of the same material (e.g. Nitinol).

In some embodiments, each of the plurality of atrial anchoring arms may be angularly offset from an adjacent ventricular anchoring leg. Additionally, or alternatively, each of the plurality of ventricular anchoring legs may be angularly offset from an adjacent atrial anchoring arm. That is, the atrial anchoring arms and ventricular anchoring legs may be situated at different rotational positions about the circumference of the annular valve body. For example, in FIG. 2B, each atrial anchoring arm 2440 and each ventricular anchoring leg 2240 may be situated at a different angular position about the circumference of annular valve body 2020. In some embodiments, the atrial anchoring arms may alternate with the ventricular anchoring legs about the circumference of the annular valve body. Additionally, or alternatively, the atrial anchoring arms may be angularly offset at a regular interval from the ventricular anchoring legs.

In some embodiments, the locations of connection between the atrial anchoring arms and annular valve body may be angularly offset from the locations of connection between the ventricular anchoring legs and annular valve body. For example, in FIG. 2A, arm attachment junctions 3202 (i.e., the locations of connection between atrial anchoring arms 2440 and annular valve body 2020) may be angularly offset from leg attachment junctions 3802 (i.e., the locations of connection between ventricular anchoring legs 2240 and annular valve body 2020). Additionally, or alternatively, the terminal arm ends of the atrial anchoring arms may be angularly offset from the terminal leg ends of the ventricular anchoring legs. For example, in FIG. 2B, terminal arm ends 2444 may be angularly offset from terminal leg ends 2244.

In some embodiments, the atrial anchoring arms and ventricular anchoring legs may be configured to extend radially outward in a direction perpendicular to the longitudinal axis of the prosthetic valve. As a result, in some embodiments, the entire length of each atrial anchoring arm may be angularly offset from the entire length of each ventricular anchoring leg. In some embodiments, "the entire length" may include the proximal end of an arm or leg, the distal end of the arm or leg, and optionally, the location of attachment of the arm or leg to the annular valve body. For example, in FIG. 2A, each atrial anchoring arm 2440, including distal arm end 2444, proximal arm end 3020, and arm attachment junction 3202, may be angularly offset from each ventricular anchoring leg 2240, including distal leg end 2244, proximal leg end 3622, and leg attachment junction 3802.

In some embodiments, a portion of at least one ventricular anchoring leg may be configured to be substantially aligned in a common lateral plane with a portion of at least one atrial anchoring arm. That is, the at least one atrial anchoring arm and at least one ventricular anchoring leg may assume a configuration in which a portion of the arm and a portion of the leg are aligned in a plane that is perpendicular to the longitudinal axis of the prosthetic valve. An example of such a configuration is illustrated in FIG. 2C, which depicts at least one ventricular anchoring leg 2240 having a portion 2246 aligned in a common lateral plane with a portion 2446 of at least one atrial anchoring arm 2440, the common lateral plane being perpendicular to the longitudinal axis 2800 illustrated in FIG. 2A. That is, leg portion 2246 and arm portion 2446 (pictured in FIG. 2C) may be positioned at the same axial position along longitudinal axis 2800. In some embodiments, atrial anchoring arms 2440 and ventricular anchoring legs 2240 may be biased to assume the configuration illustrated in FIG. 2C (e.g., due to the shape-memory properties of the arms and legs). In some embodiments, the portion of the ventricular anchoring leg that is arranged in the common lateral plane may include the terminal end of the leg; alternatively, the portion of the ventricular anchoring leg that is arranged in the common lateral plane may include a section of the leg situated radially inwards from the terminal end of the leg (such as leg portion 2246 illustrated in FIG. 2C). In some embodiments, the terminal end of the at least one atrial anchoring arm may be configured to be situated in an atrial direction relative to the portion of the atrial anchoring arm that is arranged in the common lateral plane. For example, in FIG. 2C, terminal arm end 2444 may be situated in an atrial direction from arm portion 2446 (i.e., the portion of the atrial anchoring arm that is arranged in the common lateral plane). In some embodiments, the portion of the at least one atrial anchoring arm that is arranged in the common lateral plane (e.g., portion 2446 in FIG. 3C) may be situated in an outer radial half of the at least one atrial anchoring arm.

In some embodiments, the tissue engaging portion of each atrial anchoring arm and each ventricular anchoring leg may be configured to be arranged such that when the atrial anchoring arms and ventricular anchoring legs are positioned on opposing sides of the native heart valve tissue, the native heart valve tissue assumes a serpentine arrangement between the atrial anchoring arms and the ventricular anchoring legs. As stated above, the atrial anchoring arms and ventricular anchoring legs may be biased to assume a certain configuration, such as the configuration illustrated in FIG. 2C. However, upon implantation of the prosthetic valve, the valve may grasp and retain native valve tissue between the atrial anchoring arms and ventricular anchoring legs. For example, FIGS. 10G and 10H illustrate tissue of mitral valve 9030 retained between atrial anchoring arms 2440 and ventricular anchoring legs 2240. The retained tissue may slightly deform the atrial anchoring arms 2440 and ventricular anchoring legs 2240, pushing the arms and legs axially apart from each other (and thus, out of the configuration illustrated in FIG. 2C). However, due to their shape memory characteristics, the atrial anchoring arms 2440 and ventricular anchoring legs 2240 may resist the deformation and exert a clamping force on the retained tissue. For example, atrial anchoring arms 2440 may clamp tissue by exerting a ventricularly-directed force (that is, a force directed downwards towards ventricle 9020 in FIGS. 10G and 10H) on the heart valve tissue. Similarly, ventricular anchoring legs 2240 may clamp the tissue by exerting an atrially-directed force (that is, a force directed upwards towards atrium 9010 in FIGS. 10G and 10H) on the heart valve tissue. These opposing forces may bend the native valve tissue into a zig-zagging or serpentine arrangement, in which the atrial anchoring arms 2440 press the tissue towards the ventricle 9020 and the ventricular anchoring legs 2240 press the tissue in an opposite direction towards the atrium 9010. As a result, in some embodiments, tissue in contact with one or more ventricular anchoring legs may be situated in an atrial direction (i.e., closer to atrium 9010) than tissue in contact with one or more atrial anchoring arms. Similarly, in some embodiments, tissue in contact with one or more atrial anchoring arms may be situated in a ventricular direction (i.e., closer to ventricle 9020) compared to tissue in contact with one or more ventricular anchoring legs. Opposing forces between the atrial anchoring arms and ventricular anchoring legs may also clamp or "sandwich" the heart valve tissue between the atrial anchoring arms and ventricular anchoring legs, thus firmly anchoring prosthetic heart valve 6000 within the native heart valve.

In some embodiments, an entire length of at least one ventricular anchoring leg may be configured to extend toward an atrium. In some embodiments, the entire length of at least one ventricular anchoring leg may be configured to extend toward an atrium when the at least one ventricular anchoring leg is in a radially-contracted configuration. For example, as depicted in FIG. 5A, the entire length of ventricular anchoring leg 2240 (from proximal leg end 3622 to distal leg end 2244) extends toward an atrium (i.e., in an upward direction in FIG. 5A) when the ventricular anchoring leg 2240 is in the radially-contracted configuration. Additionally, or alternatively, the entire length of at least one ventricular anchoring leg may be configured to extend toward an atrium when the at least one ventricular anchoring leg is in a radially-expanded configuration. For example, as depicted in FIG. 5E, the entire length of ventricular anchoring leg 2240 extends toward an atrium (i.e., in an upward direction in FIG. 5A) when the ventricular anchoring leg is in the radially-expanded configuration. In some embodiments, a plurality or all of the ventricular anchoring legs may be configured such that the entire length of each ventricular anchoring leg may be configured to extend towards an atrium.

In some embodiments, at least a portion of at least one atrial anchoring arm may be configured to extend toward a ventricle. For example, as depicted in FIG. 3B, an exemplary atrial anchoring arm 2440 may include an intermediate arm portion 3504 configured to extend toward a ventricle (i.e., downwards in FIG. 3B) when atrial anchoring arm 2440 is in a radially-expanded configuration. In some embodiments, atrial anchoring arm 2440 may additionally include a proximal portion 3502 and a distal portion 3506 configured to extend toward an atrium (i.e., upward in FIG. 3B) when atrial anchoring arm 2440 is in the radially-expanded configuration. In some embodiments, a portion of at least one atrial anchoring arm may be configured to extend toward an atrium, the portion of the at least one atrial anchoring arm including the terminal end of the at least one atrial anchoring arm. For example, in FIG. 3B, distal arm portion 3506, which includes terminal arm end 2444, is configured to extend toward an atrium (i.e., upward in FIG. 3B) when atrial anchoring arm 2440 is in the radially-expanded configuration. In some embodiments, and as illustrated in FIG. 5A, the entire length of atrial anchoring arm 2440 (from proximal arm end 3020 to distal arm end 2444) may be configured to extend in an atrial direction (and optionally, in a direction parallel to longitudinal axis 2800) when the arm 2440 is in a radially-contracted configuration.

In some embodiments, at least one atrial anchoring arm may include a single location of connection to the annular valve body. Additionally, or alternatively, at least one ventricular anchoring leg may include a single location of connection to the annular valve body. For example, each atrial anchoring arm and each ventricular anchoring leg may be connected to, or may otherwise extend from, a single portion of the annular valve body. For example, in FIG. 2A, each atrial anchoring arm 2440 may be connected to the annular valve body 2020 at a single arm attachment junction 3202. Additionally, or alternatively, each ventricular anchoring leg 2240 may be connected to the annular valve body 2020 at a single leg attachment junction 3802.

In various embodiments, the atrial anchoring arms and the ventricular anchoring legs may be configured to extend radially outward from separate locations of the annular valve body. That is, each location of connection may be associated with a single atrial anchoring arm or with a single ventricular anchoring leg. For example, in FIG. 2A, each arm attachment junction 3202 may be connected to a single atrial anchoring arm 2440 and each leg attachment junction 3802 may be connected to a single ventricular anchoring leg 2240.

In some embodiments, a terminal end of at least one atrial anchoring arm may be configured to extend in an atrial direction beyond an atrial end of the annular valve body. In some embodiments, the atrial end may refer to the portion of the annular valve body configured to be situated at a location within an atrium that is furthest from the adjacent ventricle, when the prosthetic valve is implanted in a native heart valve. For example, as depicted in FIG. 2A, atrial end inner frame junctions 3002 may constitute the atrial end 2024 of annular valve body 2020 because the atrial end inner frame junctions 3002 are the portions of annular valve body 2020 that are situated within atrium 9010 at a location furthest from ventricle 9020 (as shown in FIG. 10H). As shown in FIGS. 5A and 5E, terminal arm end 2444 of at least one atrial anchoring arm 2440 is configured to extend in an atrial direction beyond atrial end 2024 of the annular valve body 2020 when the prosthetic valve is in a radially-contracted configuration (FIG. 5A) and in a radially-expanded configuration (FIG. 5E). In some embodiments, the terminal arm end of at least one atrial anchoring arm may constitute the atrial end of the exemplary prosthetic valve. That is, the terminal arm end may be configured to be positioned in an atrial direction from the rest of the prosthetic valve when the prosthetic valve is in a radially-expanded configuration and in a radially-contracted configuration. Accordingly, in some embodiments, a terminal end of at least one atrial anchoring arm may be configured to be arranged in an atrial direction relative to the rest of the at least one atrial anchoring arm. For example, in FIGS. 5A and 5E, terminal arm ends 2444 may be situated in an atrial direction, relative to the rest of the atrial anchoring arms 2440.

In some embodiments, a terminal end of at least one ventricular anchoring leg may be configured to be situated in an atrial direction relative to locations of connection of the atrial anchoring arms to the annular valve body. For example, the terminal leg end of each ventricular anchoring leg may be configured to be situated in an atrial direction relative to each location of connection of the atrial anchoring arms to the annular valve body. In some embodiments, the terminal end of the at least one ventricular anchoring leg may be configured to be situated in an atrial direction relative to the locations of connection of the atrial anchoring arms to the annular valve body when the prosthetic valve is in a radially-contracted configuration. For example, as illustrated in FIG. 5A, terminal leg ends 2244 may be situated in an atrial direction relative to arm attachment junctions 3202 (i.e., the locations of connection of the atrial anchoring arms 2440 to the annular valve body 2020). Additionally, or alternatively, the terminal end of the at least one ventricular anchoring leg may be configured to be situated in an atrial direction relative to the locations of connection of the atrial anchoring arms to the annular valve body when the prosthetic valve is in a radially-expanded configuration. For example, as illustrated in FIG. 5E, terminal leg ends 2244 may be situated in an atrial direction relative to arm attachment junctions 3202.

In some embodiments, a portion of at least one ventricular anchoring leg may be configured for placement in an atrial direction relative to at least a portion of at least one atrial anchoring arm. The portion of the at least one ventricular anchoring leg may include the terminal end of the at least one ventricular anchoring leg. In some embodiments, the portion of the at least one ventricular anchoring leg may be configured for placement in an atrial direction relative to the portion of the at least one atrial anchoring arm when the prosthetic valve is arranged in a radially-contracted configuration. For example, in FIG. 5A, portions of ventricular anchoring legs 2240 that include terminal leg ends 2244 are configured for placement in an atrial direction relative to portions of the atrial anchoring arms that include arm portions 5002 and proximal arm ends 3020. Additionally, or alternatively, the portion of the at least one ventricular anchoring leg may be configured for placement in an atrial direction relative to the portion of the at least one atrial anchoring arm when the prosthetic valve is arranged in a radially-expanded configuration. In some embodiments, the portion of the at least one atrial anchoring arm may be situated in an outer radial half of the at least one atrial anchoring arm. For example, FIG. 2C illustrates an enlarged view of a terminal arm end 2444 and a terminal leg end 2244, when the prosthetic valve is arranged in a radially-expanded configuration. As illustrated in FIG. 2C, terminal leg end 2244 may be situated in an atrial direction relative to arm portion 2446. In some embodiments, arm portion 2446 may be situated in an outer radial half of atrial anchoring arm 2440, in closer proximity to distal arm end 2444 than to proximal arm end 3020.

In some embodiments, a terminal end of at least one atrial anchoring arm may be configured to be situated radially outward from terminal ends of the ventricular anchoring legs. That is, the terminal arm end of the at least one atrial anchoring arm may be configured to be positioned further away from the longitudinal axis of the prosthetic valve than the terminal leg ends of the plurality of ventricular anchoring legs. By way of example in FIG. 2E, atrial anchoring arms 2440 may be configured to extend radially outward such that the terminal arm ends 2444 form an atrial anchoring arm circumference 2640. Similarly, ventricular anchoring legs 2240 may be configured to extend radially outward such that the terminal leg ends 2244 form a ventricular anchoring leg circumference 2620. As illustrated in FIG. 2E, the atrial anchoring arm circumference 2640 may have a larger radius than the ventricular anchoring leg circumference 2620.

In some embodiments, the annular valve body may include an atrial end. In some embodiments, the atrial end may refer to the portion of the annular valve body configured to be situated at a location within the atrium that is furthest from an adjacent ventricle, when the exemplary prosthetic valve is implanted in a native heart valve. For example, as depicted in FIG. 2A, atrial end inner frame junctions 3002 may constitute the atrial end 2024 of exemplary annular valve body 2020 because the atrial end inner frame junctions 3002 are the portions of annular valve body 2020 that are situated within atrium 9010 at a location furthest from ventricle 9020 (as shown in FIG. 10H).

In some embodiments, the annular valve body may include a ventricular end opposite the atrial end of the annular valve body. In some embodiments, the ventricular end may refer to the portion of the annular valve body configured to be situated at a location within the ventricle that is furthest from an adjacent atrium, when the prosthetic valve is implanted in a native heart valve. The ventricular end of the annular valve body may constitute an opposite end of the annular valve body from the atrial end. For example, in some embodiments and as depicted in FIG. 2A, ventricular end inner frame junctions 3004 and ventricular end outer frame junctions 3604 may constitute the ventricular end 2025 of annular valve body 2020 because junctions 3004 and 3604 are the portions of annular valve body 2020 that are situated within ventricle 9020 at a location furthest from atrium 9010 (as shown in FIG. 10H). In some embodiments, the ventricular end inner frame junctions 3004 (i.e., the ventricular end of inner frame 2400) and the ventricular end outer frame junctions 3604 (i.e., the ventricular end of outer frame 2200) may be evenly aligned within a plane perpendicular to longitudinal axis 2800. That is, the ventricular end inner frame junctions 3004 and the ventricular end outer frame junctions 3604 may be situated at the same axial position along longitudinal axis 2800. In some alternative embodiments, the ventricular end inner frame junctions 3004 may constitute the ventricular end 2025 of annular valve body 2020. In some further alternative embodiments, the ventricular end outer frame junctions 3604 may constitute the ventricular end 2025 of annular valve body 2020.

In some embodiments, the annular valve body may include an intermediate portion extending between the atrial end and ventricular end of the annular valve body. In some embodiments, the intermediate portion of the annular valve body may constitute every portion of the annular valve body situated in between the atrial end of the annular valve body and the ventricular end of the annular valve body. For example, as depicted in FIG. 2A, intermediate portion 2026 of annular valve body 2020 may include every portion of the annular valve body positioned between atrial end 2024 and ventricular end 2025.

In some embodiments, the atrial anchoring arms and the ventricular anchoring legs may be configured to extend from the intermediate portion of the annular valve body. That is, the locations of connection between the atrial anchoring arms and annular valve body, as well as the locations of connection between the ventricular anchoring legs and annular valve body, may be situated within the intermediate portion of the annular valve body. For example, as illustrated in FIG. 2A, arm attachment junctions 3202 (from which atrial anchoring arms 2440 extend) and leg attachment junctions 3802 (from which ventricular anchoring legs 2240 extend) are situated in the intermediate portion 2026 of annular valve body 2020, and are accordingly spaced apart from the atrial end 2024 and ventricular end 2025 of the annular valve body. In some embodiments, the arm attachment junctions 3202 may be situated in an atrial direction relative to the leg attachment junctions 3802.

In various embodiments of the present disclosure, the annular valve body may be formed at least partially of a plurality of supporting members or struts. In some embodiments, the struts may intersect at junctions to form a wire mesh, stent-like, or cage-like structure of the annular valve body. In some embodiments, the struts of the annular valve body may be made of one or more metals or alloys, such as Nitinol. In some embodiments, the struts of the annular valve body may meet or intersect at junctions of the annular valve body. For example, as illustrated in FIG. 2A, annular valve body 2020 may include inner frame atrial struts 3008*a*, inner frame intermediate struts 3008*b*, and inner frame ventricular struts 3008*c* intersecting at atrial end inner frame junctions 3002, arm attachment junctions 3202, inner frame junctions 3204, and ventricular end inner frame junctions 3004, which may form an inner frame tubular portion 3005 of the annular valve body 2020 (as illustrated in FIG. 3A). Additionally, or alternatively, annular valve body 2020 may include outer frame atrial circumferential struts 3608*a*, outer frame leg base struts 3608*b*, and outer frame ventricular circumferential struts 3608*c* intersecting at atrial end outer frame junctions 3602, leg attachment junctions 3802, outer frame junctions 3804, and ventricular end outer frame junctions 3604, which may form an outer frame tubular portion 3605 of the annular valve body 2020 (as illustrated in FIG. 3C). A junction may be formed at a location at which at least two struts terminate; that is, exemplary struts may extend to and terminate at a junction at which they intersect with one or more other struts. In some embodiments, the struts may intersect at junctions to form a lattice or overlapping pattern. In some embodiments, two struts, three struts, four struts, five struts, or any other suitable number of struts may intersect at junctions of the annular valve body.

In some embodiments, the annular valve body may include an atrial end formed by one or more junctions. That is, two or more struts may intersect at a junction that forms the atrial end of the annular valve body. For example, as illustrated in FIG. 2A, inner frame atrial struts 3008*a* may intersect at atrial end inner frame junctions 3002, which may form the atrial end 2024 of the annular valve body 2020. Additionally, or alternatively, the annular valve body may include a ventricular end formed by one or more junctions. That is, two or more struts of the annular valve body may intersect at a junction that forms the ventricular end of the annular valve body. For example, as illustrated in FIG. 2A, inner frame ventricular struts 3008*c* may intersect at ventricular end inner frame junctions 3004, while outer frame leg base struts 3608*b* and outer frame ventricular circumferential struts 3608*c* may intersect at ventricular end outer frame junctions 3604. In some embodiments, ventricular end inner frame junctions 3004 and ventricular end outer frame junctions 3604 may form the ventricular end 2025 of the annular valve body 2020. Additionally, or alternatively, the annular valve body may include one or more intermediate junctions positioned within the intermediate portion of the annular valve body, between the atrial junctions and ventricular junctions. For example, as illustrated in FIG. 2A, annular valve body 2020 may include intermediate junctions including arm attachment junctions 3202, inner frame junctions 3204, atrial end outer frame junctions 3602, leg attachment junctions 3802, and outer frame junctions 3804.

In some embodiments, the atrial anchoring arms may extend from intermediate junctions of the annular valve body. Additionally, or alternatively, the ventricular anchoring legs may extend from intermediate junctions of the annular valve body. For example, as illustrated in FIG. 2A, arm attachment junctions 3202 (from which atrial anchoring arms 2440 extend) and leg attachment junctions 3802 (from which ventricular anchoring legs 2240 extend) constitute intermediate junctions of the annular valve body 2020, and are accordingly spaced apart from the atrial end inner frame junctions 3002 (i.e., the atrial junctions of annular valve body 2020) and from the ventricular end inner frame junctions 3004 and ventricular end outer frame junctions 3604 (i.e., the ventricular junctions of annular valve body 2020).

In some embodiments, the exemplary prosthetic valve may include an annular outer frame and an inner frame situated at least partially within the annular outer frame. In some embodiments, one or both of the inner frame and the outer frame may be annular, and the inner frame may be positioned within an opening of the outer frame. For example, FIG. 2A depicts an exemplary prosthetic valve frame 2000 including an outer frame 2200 and an inner frame 2400 situated at least partially within outer frame 2200. In some alternative embodiments, the inner frame may be situated entirely within the outer frame. One or both of the inner frame and the outer frame may be configured to radially expand between a radially-contracted configuration (e.g., a crimped state) and a radially-expanded configuration. In some embodiments, the inner frame may be configured to receive or otherwise support a flow control device, such as one or more leaflets, for regulating flow of blood or other bodily fluids through the prosthetic valve.

In some embodiments, the plurality of atrial anchoring arms may be configured to extend from the inner frame. Additionally, or alternatively, the plurality of ventricular anchoring legs may be configured to extend from the annular outer frame. For example, FIG. 3A depicts atrial anchoring arms 2440 extending from inner frame 2400, and FIG. 3C depicts ventricular anchoring legs 2240 extending from outer frame 2200. In some embodiments, the atrial anchoring arms and the ventricular anchoring legs may be physically connected to the inner frame and annular outer frame, respectively, such as by welding or adhesive. In some alternative embodiments, the atrial anchoring arms and the ventricular anchoring legs may be integrally formed with the inner frame and annular outer frame, respectively.

In some embodiments, the inner frame may have a greater axial length than the expandable annular outer frame, relative to the longitudinal axis of the exemplary prosthetic valve. In some embodiments, the inner frame, including the inner frame tubular portion and the plurality of atrial anchoring arms, may have a greater axial length than the outer frame, including the outer frame tubular portion and the plurality of ventricular anchoring legs. For example, in the embodiment depicted in FIG. 2D, device height 2560 may represent the axial length of inner frame 2400, including inner frame tubular portion 3005 and atrial anchoring arms 2440. Similarly, outer frame height 2550 may represent the axial length of outer frame 2200, including outer frame tubular portion 3605 and ventricular anchoring legs 2240. As illustrated in FIG. 2D, device height 2560 may be greater than outer frame height 2550.

Additionally, or alternatively, the inner frame tubular portion may have a greater axial length than the outer frame tubular portion, relative to the longitudinal axis of the exemplary prosthetic heart valve. In some embodiments, the inner frame tubular portion and outer frame tubular portion may together constitute the annular valve body. For example, in the embodiment depicted in FIG. 2D, inner frame tubular portion height 2530 may represent the axial length of inner frame tubular portion 3005. Inner frame tubular portion height 2530 may extend axially between atrial end inner frame junctions 3002 and ventricular end inner frame junctions 3004. Similarly, outer frame tubular portion height 2570 may represent the axial length of outer frame tubular portion 3605. Outer frame tubular portion height 2570 may extend axially between atrial end outer frame junctions 3602 and ventricular end outer frame junctions 3604. As illustrated in FIG. 2D, inner frame tubular portion height 2530 may be greater than outer frame tubular portion height 2570. In some embodiments, the ventricular ends of the inner frame and outer frame may be substantially aligned in a common lateral plane; that is, the ventricular ends of the inner frame and outer frame may be arranged along a plane perpendicular to the longitudinal axis of the prosthetic heart valve. For example, in FIG. 2D, ventricular end inner frame junctions 3004 may be substantially aligned in a common lateral plane with ventricular end outer frame junctions 3604. Further, the atrial end of the inner frame may extend in an atrial direction beyond the atrial end of the outer frame (that is, the atrial end of the inner frame may be positioned above the atrial end of the outer frame in FIG. 2D). For example, in FIG. 2D, the atrial end inner frame junctions 3002 may be positioned in an atrial direction from the atrial end outer frame junctions 3602.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A prosthetic valve for implantation within a native heart valve, the prosthetic valve configured to transition from a radially-contracted delivery configuration to a radially-expanded deployed configuration, the prosthetic valve comprising:

an annular valve body having a tubular annulus;

a plurality of atrial anchoring arms configured to extend radially outward from the annular valve body, each of the plurality of atrial anchoring arms having a native valve tissue engaging portion;

a plurality of ventricular anchoring legs configured to extend radially outward from the annular valve body, each of the plurality of ventricular anchoring legs having a native valve tissue engaging portion; and a fluid-impermeable cuff extending around at least a portion of the annular valve body, a portion of the fluid-impermeable cuff being positioned between the plurality of atrial anchoring arms and the plurality of ventricular anchoring legs, wherein each of the plurality of atrial anchoring arms is angularly offset from an adjacent ventricular anchoring leg, and when the prosthetic valve is arranged in the deployed configuration, the tissue engaging portion of at least one atrial anchoring arm is configured to be situated in a ventricular direction from the tissue engaging portion of at least one ventricular anchoring leg such that the portion of the fluid-impermeable cuff assumes a serpentine arrangement between the atrial anchoring arms and the ventricular anchoring legs.

2. The prosthetic valve of claim 1, wherein an entire length of the at least one ventricular anchoring leg is configured to extend toward an atrium.

3. The prosthetic valve of claim 1, wherein at least a portion of the at least one atrial anchoring arm is configured to extend toward a ventricle.

4. The prosthetic valve of claim 1, wherein the at least one atrial anchoring arm has a single location of connection to the annular valve body and the at least one ventricular anchoring leg has a single location of connection to the annular valve body.

5. The prosthetic valve of claim 1, wherein the atrial anchoring arms and the ventricular anchoring legs are configured to extend radially outward from separate locations of the annular valve body.

6. The prosthetic valve of claim 1, wherein a terminal end of the at least one atrial anchoring arm is configured to extend in an atrial direction beyond an atrial end of the annular valve body.

7. The prosthetic valve of claim 1, wherein a terminal end of the at least one atrial anchoring arm is configured to be situated in an atrial direction relative to the rest of the at least one atrial anchoring arm.

8. The prosthetic valve of claim 1, wherein a terminal end of the at least one ventricular anchoring leg is configured to be situated in an atrial direction relative to locations of connection of the atrial anchoring arms to the annular valve body.

9. The prosthetic valve of claim 1, wherein a portion of the at least one atrial anchoring arm is configured to extend toward an atrium, the portion of the at least one atrial anchoring arm including the terminal end of the at least one atrial anchoring arm.

10. The prosthetic valve of claim 1, wherein a portion of the at least one ventricular anchoring leg is configured to be substantially aligned in a common lateral plane with a portion of the at least one atrial anchoring arm.

11. The prosthetic valve of claim 10, wherein the portion of the at least one ventricular anchoring leg is a terminal end of the at least one ventricular anchoring leg.

12. The prosthetic valve of claim 10, wherein a terminal end of the at least one atrial anchoring arm is configured to be situated in an atrial direction relative to the portion of the at least one atrial anchoring arm.

13. The prosthetic valve of claim 10, wherein the portion of the at least one atrial anchoring arm is situated in an outer radial half of the at least one atrial anchoring arm.

14. The prosthetic valve of claim 1, wherein a portion of the at least one ventricular anchoring leg is configured for placement in an atrial direction relative to at least a portion of the at least one atrial anchoring arm.

15. The prosthetic valve of claim 14, wherein the portion of the at least one atrial anchoring arm is situated in an outer radial half of the at least one atrial anchoring arm.

16. The prosthetic valve of claim 1, wherein a terminal end of the at least one atrial anchoring arm is configured to be situated radially outward from terminal ends of the ventricular anchoring legs.

17. The prosthetic valve of claim 1,
wherein the annular valve body further includes an atrial end, a ventricular end opposite the atrial end, and an intermediate portion extending between the atrial end and the ventricular end; and
wherein the atrial anchoring arms and the ventricular anchoring legs are configured to extend from the intermediate portion of the annular valve body.

18. The prosthetic valve of claim 17,
wherein the annular valve body additionally includes a plurality of struts intersecting at junctions,
wherein the atrial end of the annular valve body includes a plurality of atrial junctions,
wherein the ventricular end of the annular valve body includes a plurality of ventricular junctions, and
wherein the intermediate portion of the annular valve body includes a plurality of intermediate junctions, the atrial anchoring arms and ventricular anchoring legs extending from intermediate junctions.

19. The prosthetic valve of claim 1, further comprising:
an annular outer frame; and
an inner frame situated at least partially within the annular outer frame,
wherein the atrial anchoring arms extend from the inner frame and the ventricular anchoring legs extend from the annular outer frame.

20. The prosthetic valve of claim 19, wherein the inner frame has a greater axial length than a length of the annular outer frame.

21. The prosthetic valve of claim 1, wherein the portion of the fluid-impermeable cuff includes a cuff sheet extending circumferentially around the annular valve body.

22. The prosthetic valve of claim 21, wherein the cuff sheet is configured to be situated in an atrial direction from the tissue engaging portion of the at least one ventricular anchoring leg and in a ventricular direction from the tissue engaging portion of the at least one atrial anchoring arm.

23. The prosthetic valve of claim 1, further comprising:
a skirt layer extending around an external surface of at least a portion of the annular valve body, wherein the skirt layer extends to a ventricular end of the annular valve body and is connected to the fluid-impermeable cuff.

24. The prosthetic valve of claim 1,
wherein the fluid-impermeable cuff comprises a first cuff sheet connected to a second cuff sheet, and
wherein the first cuff sheet and the second cuff sheet are configured to extend around a terminal end of the at least one atrial anchoring arm.

* * * * *